US012797318B2

(12) United States Patent
Magee et al.

(10) Patent No.: US 12,797,318 B2
(45) Date of Patent: Nov. 17, 2026

(54) HAIR TREATMENT SERUM AND METHOD OF USE

(71) Applicant: L'OREAL, Paris (FR)

(72) Inventors: Rachel N. Magee, Westfield, NJ (US); Kazumitsu Kawakami, Kawasaki (JP)

(73) Assignee: L'OREAL, Paris (FR)

( * ) Notice: Subject to any disclaimer, the term of this patent is extended or adjusted under 35 U.S.C. 154(b) by 274 days.

(21) Appl. No.: 18/618,507

(22) Filed: Mar. 27, 2024

(65) Prior Publication Data

US 2025/0302716 A1 Oct. 2, 2025

(51) Int. Cl.

| | |
|---|---|
| ***A61K 8/44*** | (2006.01) |
| ***A61K 8/06*** | (2006.01) |
| ***A61K 8/31*** | (2006.01) |
| ***A61K 8/37*** | (2006.01) |
| ***A61K 8/58*** | (2006.01) |
| ***A61K 8/73*** | (2006.01) |
| ***A61K 8/81*** | (2006.01) |
| ***A61Q 5/12*** | (2006.01) |

(52) U.S. Cl.

CPC ................ *A61K 8/44* (2013.01); *A61K 8/062* (2013.01); *A61K 8/31* (2013.01); *A61K 8/37* (2013.01); *A61K 8/585* (2013.01); *A61K 8/731* (2013.01); *A61K 8/8147* (2013.01); *A61Q 5/12* (2013.01); *A61K 2800/48* (2013.01); *A61K 2800/5426* (2013.01); *A61K 2800/596* (2013.01); *A61K 2800/805* (2013.01)

(58) Field of Classification Search

None

See application file for complete search history.

(56) References Cited

U.S. PATENT DOCUMENTS

| | | | | |
|---|---|---|---|---|
| 9,801,807 | B2 | 10/2017 | Trumbore et al. | |
| 11,890,360 | B1 | 2/2024 | Zecchino et al. | |
| 2004/0052865 | A1 | 3/2004 | Gower et al. | |
| 2004/0063616 | A1 | 4/2004 | Patt | |
| 2006/0165636 | A1 * | 7/2006 | Hasebe .................... | A61K 8/88 424/70.14 |
| 2008/0148689 | A1 | 6/2008 | Xia et al. | |

(Continued)

FOREIGN PATENT DOCUMENTS

| | | |
|---|---|---|
| JP | 2005139139 A | 6/2005 |
| JP | 2009079027 A | 4/2009 |

OTHER PUBLICATIONS

Preliminary Search Report and Written Opinion issued on Jan. 9, 2025 for corresponding French Application No. FR 2406095.

(Continued)

*Primary Examiner* — Dominic Lazaro
(74) *Attorney, Agent, or Firm* — POLSINELLI PC

(57) ABSTRACT

The instant disclosure is drawn to a hair treatment serum that provides softness, moisturization, and additional conditioning benefits to hair. The hair treatment serum includes: (a) a polyglutamic acid, a salt thereof, or a combination thereof; (b) one or more oils, wherein at least one of the one or more oils is a hydrocarbon oil; (c) one or more thickening agents, wherein at least one of the one or more thickening agents is a polyacrylic acid thickening agent; and (d) water. The serum is preferably an oil-in-water emulsion or oil-in-water dispersion. The hair treatment serum is particularly useful in methods for smoothing, hydrating, and conditioning hair.

19 Claims, 2 Drawing Sheets

(56) References Cited

U.S. PATENT DOCUMENTS

| | | | | |
|---|---|---|---|---|
| 2011/0117219 | A1* | 5/2011 | Springer | A61Q 5/006 514/408 |
| 2012/0301436 | A1 | 11/2012 | Yang et al. | |
| 2014/0335038 | A1* | 11/2014 | Bhogal | A61K 8/22 424/70.14 |
| 2015/0209243 | A1 | 7/2015 | Shiroya et al. | |
| 2015/0314004 | A1 | 11/2015 | Li | |
| 2017/0100327 | A1 | 4/2017 | Allen | |
| 2017/0273875 | A1 | 9/2017 | Liu et al. | |
| 2018/0369080 | A1 | 12/2018 | Kasai et al. | |
| 2018/0369106 | A1 | 12/2018 | Kasai et al. | |
| 2020/0155426 | A1 | 5/2020 | Shiroya et al. | |
| 2020/0163864 | A1 | 5/2020 | Shiroya et al. | |
| 2020/0163866 | A1 | 5/2020 | Shiroya et al. | |
| 2020/0330363 | A1 | 10/2020 | Shiroya et al. | |
| 2022/0186090 | A1 | 6/2022 | Sieverding | |
| 2024/0009644 | A1 | 1/2024 | Ji et al. | |

OTHER PUBLICATIONS

Database GNPD [Online] Mintel; anonymous: “Hair & Nature Moisture Hair Lotion”, 2012 XP093237057.

Database GNPD [Online] Mintel; anonymous: “Curling Essence”, 2017 XP093237058.

* cited by examiner

Inventive Serum A | Comparative Serum 2 | Comparative Serum 3

Comparative Serum 4

Inventive Serum A

HAIR TREATMENT SERUM AND METHOD OF USE

FIELD OF THE DISCLOSURE

The instant disclosure is drawn to a hair treatment serum containing γ-polyglutamic acid, a salt thereof, or a combination thereof. The hair treatment serum provides softness, moisturization, and other conditioning benefits to hair.

BACKGROUND

Consumers desire new multi-functional hair products that impart quality styling benefits to hair but simplify their routine. Such products should be pleasing to the senses, incorporate innovative technologies, and perform better than currently available products. Furthermore, consumers prefer hair care products that are light in texture, easy to apply, and provide long-term protection and nourishing attributes to the hair.

Products that condition hair come in various types, each catering to different needs and preferences. Some common types of conditioning products include rinse-out conditioners, leave-in conditioners, deep conditioners, oil treatments, and co-washes. Rinse-out conditioners are the most common type of conditioning product. They are applied after cleansing the hair with a shampoo and are rinsed from the hair before drying and styling the hair. Rinse-out conditioners typically remain in the hair for only a few minutes before being rinsed from the hair yet they are suitable for most hair types and can be used daily or as needed.

Leave-in conditioners are usually applied to the hair after washing the hair with a shampoo and are not rinsed out. They remain on the hair during drying and styling and are designed to provide long-lasting moisturization and nourishment, making them a popular choice for dry or damaged hair. Leave-in conditioners can also offer additional benefits such as heat protection, frizz control, and detangling. They are especially useful for those who style their hair frequently or need extra hydration throughout the day.

Deep conditioners and oil treatments are intensive treatments designed to provide deep hydration and repair to the hair. They are usually applied after shampooing and remain on the hair for a longer duration than a typical rinse-out conditioner. Heat is sometimes used to enhance their effects. Consumers rely on deep conditioners and oil treatment to treat dry, damaged, or chemically treated hair. The goal is to restore moisture, repair or mitigate damage, and improve overall hair health and appearance.

All-in-one shampoo/conditioner products (also known as "co-wash" products or "conditioning shampoos") attempt to combine the cleansing benefits of a shampoo with the conditioning properties of a conditioner. They proport to cleanse the hair while simultaneously conditioning the hair, making them a convenient and simplified hair care routine. Cleansing compositions, like shampoos, are designed to remove sebum, oil, and debris from the hair, which is antithetical to conditioning. Many conditioning products are designed to impart oil and other conditioning agents to the hair. Furthermore, effective shampoos cause the cuticle of the hair to open helping to release and remove debris. Effective conditioning products, on the other hand, are designed to close the cuticle to prevent release of moisture and to provide added protection to the hair. A single product cannot open and close the cuticle at the same time.

Conditioning products on the market appear in various forms, for example, solutions, lotions, creams, sprays, oils, and even aerosols. Regardless of the form, consumers seek products that are lightweight so they do not weigh down the hair or leave the hair with a greasy or oily texture. Conditioned hair should look natural and healthy, have a pleasant shine, and flow naturally. Ideal conditioning products moisturize the hair, provide protection from heat and other environmental damage, and control frizz and flyaways.

The hair treatment serum of the instant disclosure provides the above-mentioned benefits. In addition, the hair treatment serum is fast acting and quickly absorbs deep into the hair fibers. Hair treated with the hair treatment serum is soft, well-hydrated, and smooth, exhibits improved hair elasticity, and enjoys protections from damage and future breakage.

SUMMARY OF THE DISCLOSURE

The instant disclosure is drawn to a stable hair treatment serum that provides long-lasting softness, moisturization, and other conditioning properties to the hair. The hair treatment serum includes polyglutamic acid, a salt thereof, or combinations thereof, which enhances the serum's conditioning benefits. In addition, the serum includes one or more hydrocarbon oils and one or more polyacrylic acid thickening agents. The hydrocarbon oils are lightweight and contribute to the serum's moisturizing properties. The polyacrylic acid thickener is multifunctional. It adds viscosity, contributes to the stability of the serum, and beneficially interacts with other ingredients resulting in a serum that is surprisingly effective. Without wishing to be bound by any particular theory, the inventors believe that the combination of the one or more hydrocarbon oils, the polyacrylic acid thickening agent, and the polyglutamic acid, salts thereof, or combinations thereof is an important aspect of the hair treatment serum. Upon application to the hair, the serum forms smooth, flexible, and durable films. The films prevent moisture loss, protect against heat and other environmental damage, and control frizz. The films are surprisingly lightweight, flexible, and long-lasting, and do not become sticky or heavy, resulting in the hair having a healthy sheen and moisturized appearance.

The hair treatment serum typically includes:

(a) polyglutamic acid, a salt thereof, or a combination thereof;

(b) one or more oils, wherein at least one of the one or more oils is a hydrocarbon oil;

(c) one or more thickening agents, wherein at least one of the one or more thickening agents is a polyacrylic acid thickening agent; and (d) water;

wherein the serum is an oil-in-water emulsion or oil-in-water dispersion, and all percentages by weight are based on the total weight of the serum.

Nonlimiting examples of polyglutamic acid include α-polyglutamic acid, γ-polyglutamic acid, salts thereof, or mixtures thereof. Nonlimiting examples of γ-polyglutamic acid and salts thereof include γ-polyglutamic acid, sodium γ-polyglutamate, potassium γ-polyglutamate, calcium γ-polyglutamate, magnesium γ-polyglutamate, and zinc γ-polyglutamate. Sodium γ-polyglutamate and potassium γ-polyglutamate are particularly preferred.

The hair treatment serum may include a variety of different oils. Useful oils include oils of plant origin, oils of animal original, synthetic oils, hydrocarbon oils, ester oils, silicone oils, fatty alcohols, and liquid triglycerides. Nonetheless, at least one of the one or more oils is preferably a hydrocarbon oil. Nonlimiting examples of hydrocarbon oils include C13-15 alkane, hydrogenated polydecene, hydrogenated polyisobutene, isododecane, isohexadecane, squalane, undecane, tridecane, C13-14 alkane, C14-17 alkane, C14-19 alkane, C15-19 alkane, or mixtures thereof. In a preferred embodiment, the hair treatment serum includes one or more hydrocarbon oils selected from squalane, liquid paraffin, C12-15 alcohol benzoates, hydrogenated polyisobutene, and hydrogenated polydecene. In addition to one or more hydrocarbon oils, the hair treatment serum preferably also includes one or more ester oils, one or more silicone oils, or combinations thereof.

Nonlimiting examples of ester oils include cetyl ethylhexanoate, hexyldecyl ethylhexanoate, isocetyl myristate, isotridecyl isononanoate, pentaerythrityl tetraisostearate, pentaerythrityl tetraethylhexanoate, triethylhexanoin, caprylic/capric triglyceride, coco-caprylate/caprate, dicaprylyl carbonate, phytosteryl/octyldodecyl lauroyl glutamate, trimethylolpropane tricaprylate/tricaprate, dipentaerythrityl hexa C5-9 acid esters, diisostearyl malate, hexyl laurate, neopentyl glycol diheptanoate, ethyl isostearate, isopropyl myristate, isostearyl isostearate, and octyldodecyl myristate.

Nonlimiting examples of silicone oils include dimethicone, dimethiconol, cyclopentasiloxane, cyclomethicone, cyclotetrasiloxane, cyclohexasiloxane, cycloheptasiloxane, decamethylcyclopentasiloxane, cyclotetrasiloxane, cyclotrisiloxane, capryldimethicone, caprylyl trimethicone, caprylyl methicone, cetearylmethicone, hexadecylmethicone, hexylmethicone, lauryl methicone, myristyl methicone, phenyl methicone, stearyl methicone, stearyl dimethicone, behenyl dimethicone, trifluoropropyl methicone, cetyl dimethicone, polyphenylmethylsiloxane, dimethylpolysiloxane, methylphenylpolysiloxane, methyltrimethicone, diphenylsiloxyphenyl trimethicone, and phenyl trimethicone, and mixtures thereof.

Nonlimiting examples of thickening agents include thickening polymers, such as anionic, cationic, amphoteric, and nonionic thickening polymers, and non-polymeric thickening agents such as mineral thickening agents such as clays (e.g., smectite, hectorite, and montmorillonite, etc.). At least one of the one or more thickening agents is preferably a polyacrylic acid thickening agent, for example, crosslinked acrylic acid polymers known as carbomers.

The hair treatment serum preferably includes one or more polysaccharide thickening agents. Nonlimiting examples of polysaccharide thickening agents include starches, modified starches, gums, modified gums, celluloses, modified cellulose, guar gums, modified guar gums, derivatives thereof, or mixtures thereof. More specific nonlimiting examples of polysaccharide thickening agents include starch, modified starch, xanthan gum, gellan gum, *sclerotium* gum, guar gum, hydroxypropyl guar, hydroxyethylcellulose, hydroxypropylcellulose, hydroxyethylmethylcellulose, hydroxypropylmethylcellulose, carboxymethyl cellulose, derivatives thereof, or a combination thereof.

In a particularly preferred embodiment, the hair treatment serum includes both a polyacrylic acid thickening agent and a polysaccharide thickening agent, especially one or more polysaccharide thickening agents selected from guar gum, guar derivatives (e.g., hydroxypropyl guar), starch, and starch derivatives, for example, starch derivatives selected from cornstarch, potato starch, tapioca, arrowroot, wheat starch, and rice starch.

The hair treatment serum is typically an oil-in-water emulsion or oil-in-water dispersion. The aqueous phase of the serum is predominantly water. Nonetheless, the aqueous phase may also include one or more water soluble organic solvents, pH adjusting agents, buffers, salts, water-soluble active ingredients, aqueous thickening agents, and the like. In various embodiments, the hair treatment serum includes about 50 to about 95 wt. % of water, preferably about 75 to about 95 wt. % water, and more preferably about 80 to about 92 wt. % of water.

The hair treatment serum typically includes one or more surfactants, for example, one or more cationic surfactants, one or more amphoteric surfactants, one or more nonionic surfactants, one or more anionic surfactants, or combinations thereof. Preferably, the hair treatment serum includes one or more nonionic surfactants, one or more amphoteric surfactants, one or more cationic surfactants, or combinations thereof. Cationic surfactants are particularly useful for their conditioning properties.

The hair treatment serum optionally includes one or more cationic conditioning polymers. Nonlimiting examples of cationic conditioning polymers include polyquaterniums, cationic polysaccharide derivatives, cationic gum derivatives, polymer derivatives of diallyldimethyl ammonium chloride, polymer derivatives of methacrylamidopropyltrimethylammonium chloride, cationic cellulose derivatives, quaternized hydroxyethyl cellulose, cationic starch derivatives, cationic guar gum derivatives (hydroxypropyl guar hydroxypropyltrimonium chloride), copolymers of acrylamide and dimethyldiallyammonium chloride. Preferably, the hair treatment serum includes one or more polyquaterniums, in particular, polyquaternium-4, polyquaternium-7, polyquaternium-10, or mixtures thereof.

The hair treatment serum is useful in methods for treating hair, for example, methods for conditioning hair, methods for smoothing hair, methods for styling hair, or combinations thereof. The hair treatment serum can be formulated and used as a leave-in product or formulated and used as a rinse-out product. Preferably, however, the hair treatment serum is a leave-on product, which is applied to hair, for example, wet or damp hair. After application of the wet or damp hair, the hair treatment serum is allowed to dry naturally or can be forcibly dried, for example, with a blow dryer. The hair treatment serum is used in methods for conditioning hair, strengthening hair, protecting hair from damage, including damage from heat, controlling frizz, imparting shine, and protecting artificially color hair from color fading.

BRIEF DESCRIPTION OF DRAWINGS

Implementation of the present technology is described, by way of example only, with reference to the attached figures, wherein.

Figure 1:
FIG. 1 is a photograph comparing a hair swatch treated with an inventive serum and two hair swatches treated with a variety of different comparative serums.

The various aspects of the disclosure are not limited to the results, arrangements,

DETAILED DESCRIPTION OF THE DISCLOSURE

The instant case is drawn to a hair treatment serum that provides softness, moisturization, and conditioning benefits to hair and to methods for treating the hair with the hair treatment serum. The hair treatment serum is typically used as a leave-in product. Use of the hair treatment serum prevents split ends, speeds drying and styling time, improves hairs' strength and resilience, and imparts softness and shine to the hair. The hair treatment serum includes:

(a) about 0.05 to about 2 wt. % of polyglutamic acid, a salt thereof, or a combination thereof;

(b) about 2 to about 10 wt. % of one or more oils, wherein at least one of the one or more oils is (b)(i) a hydrocarbon oil;

(c) about 0.1 to about 3 wt. % of one or more thickening agents, wherein at least one of the one or more thickening agents is (c)(i) a polyacrylic acid thickening agent;

(d) water;

(e) optionally, one or more surfactants; and (f) optionally, one or more cationic thickening polymers;

(g) optionally, about 0.01 to about 10 wt. % of one or more miscellaneous ingredients;

wherein the hair treatment serum is an oil-in-water emulsion or oil-in-water dispersion; and all percentages by weight are based on the total weight of the hair treatment serum.

It can be beneficial for the weight ratio of the polyglutamic acid, salt thereof, or combination thereof of (a) and the one or more hydrocarbon oils of (b)(i) to be from about 1:1 to about 1:25, preferably from about 1:1 to about 1:10, more preferably from about 1:2 to about 1:5 ((a):(b)(i)).

It can also be beneficial for the weight ratio of the polyglutamic acid, salt thereof, or combination thereof of (a) and the one or more polyacrylic acid thickening agents of (c)(i) to be from about 1:1 to about 1:25, preferably from about 1:1 to about 1:10, more preferably from about 1:2 to about 1:5 ((a):(c)(i)).

Moreover, it can be beneficial for the weight ratio of the one or more hydrocarbon oils of (b)(i) to the one or more polyacrylic acid thickening agents of (c)(i) to be from about 1:5 to about 5:1, preferably from about 1:3 to about 3:1, more preferably from about 1:2 to about 2:1 ((b)(i):(c)(i)).

The pH of the hair treatment serum will vary. Nonetheless, it typically has an acidic pH, i.e., a pH of less than 7. Hair itself is naturally acidic, having a pH from about 3.5 to about 4.5. The natural pH of the scalp is roughly about 5.5, which is slightly higher than the pH of the hair. The acidic pH of the hair treatment serum is useful for maintaining the natural pH of the hair and scalp, which is optimal. Various treatments to hair such as oxidative coloring, bleaching, chemical shaping, and even shampooing can disrupt the natural pH of the hair and scalp and lead to dryness, frizz, and even dandruff. Preferably, the pH of the hair treatment serum is from about 4.5 to about 6.5, more preferably from about 5 to about 6.5, and even more preferably from about 5.5 to about 6.5.

The viscosity of the hair treatment serum will vary. Nonetheless, in certain embodiments, the viscosity of the hair treatment serum is from about 10 to about 20,000 cP at 25° C. measured with a Brookfield DV-LL+ Pro Viscometer using Helipath Spindle T-C 93 and rotational speed of 5% RPM. The viscosity of the hair treatment serum is preferably from about 100 to about 15,000 cP, more preferably from about 1,000 to about 12,000 cP, and even more preferably from about 5,000 to about 10,000 cP at 25° C. measured with a Brookfield DV-LL+ Pro Viscometer using Helipath Spindle T-C 93 and rotational speed of 5% RPM.

(a) Polyglutamic Acid, Salts Thereof, Combinations Thereof

Polyglutamic acid is a polymer of the amino acid, glutamic acid. Depending on where the individual monomers connect to one another, polyglutamic acid can be gamma polyglutamic acid (γ-polyglutamic acid), the form where the peptide bonds are between the amino group of glutamic acid and the carboxyl group at the end of the glutamic acid side chain, or alpha polyglutamic acid, the form where the alpha-carboxyl is used to form the peptide bond. Preferably, the polyglutamic acid is α-polyglutamic acid, γ-polyglutamic acid, salts thereof, or mixtures thereof. More preferably, the polyglutamic acid is γ-polyglutamic acid, salts thereof, or mixtures thereof.

Nonlimiting examples of γ-polyglutamic acid and salts of γ-polyglutamic acid include γ-polyglutamic acid, sodium γ-polyglutamate, potassium γ-polyglutamate, calcium γ-polyglutamate, magnesium γ-polyglutamate, and zinc γ-polyglutamate. Sodium γ-polyglutamate and potassium γ-polyglutamate are particularly preferred.

The total amount of the polyglutamic acid, salts thereof, or combinations thereof will vary but is typically from about 0.05 to about 2 wt. %, based on the total weight of the hair treatment serum. In further embodiments, the hair treatment serum includes about 0.05 to about 1.5 wt. %, about 0.05 to about 1.2 wt. %, about 0.05 to about 1 wt. %, about 0.05 to about 0.8 wt. %, about 0.05 to about 0.5 wt. %, about 0.1 to about 2 wt. %, about 0.1 to about 1.5 wt. %, about 0.1 to about 1.2 wt. %, about 0.1 to about 1 wt. %, or about 0.1 to about 0.5 wt. % of polyglutamic acid, salts thereof, or combinations thereof, based on the total weight of the hair treatment serum. In a preferred embodiment, the hair treatment serum includes from about 0.05 to about 1.2 wt. %, preferably about 0.1 to about 1 wt. %, more preferably about 0.1 to about 0.8 wt. % of polyglutamic acid, salts thereof, or combinations thereof, based on the total weight of the hair treatment serum.

(b) Oils and Oil Phase

The term "oil" is understood to mean a compound or blend of compounds that is liquid at ambient temperature (25° C.) and normal pressure (1 atm) and is not soluble when added into water at ambient temperature and normal pressure in an amount of 1% or is only soluble to a level of less than 10% by weight, with respect to the weight of oil introduced into the water. For purposes of the instant disclosure, the one or more oils may include fatty compounds that are not individually liquid at ambient temperature (25° C.) and normal pressure (1 atm) but can exist as a liquid when combined with additional oils of the hair treatment serum. For example, individual fatty alcohols such as cetyl alcohol, stearyl alcohol, and behenyl alcohol, and waxes are solid at room temperature. Nonlimiting examples of waxes that may be included in the oil phase include Candelilla wax, bees wax, microcrystalline wax, copernicia cerifera (Carnauba) wax, derivatives thereof, or mixtures there. Therefore, they do not individually constitute an oil. Nonetheless, solid fatty alcohols and other solid fatty compounds such as waxes can be dissolved in oils, for example, with heating, and the resulting blend is a liquid at room temperature (the resulting blend is an "oil"). Therefore, the "one or more oils" of the instant disclosure can include one or more solid fatty compounds provided that the one or more solid fatty compounds exists as an oil (liquid) in the hair treatment serum.

The hair treatment serum is typically an oil-in-water emulsion or oil-in-water dispersion. The one or more oils form part of oil phase (also referred to as "fatty phase," "lipophilic phase, or "hydrophobic phase"). The oil phase includes the one or more oils and the ingredients that are soluble in the oil phase, for example, lipophilic vitamins, certain organic solvents, etc.

The one or more oils may include non-volatile oils, one or more volatile oils, or combinations thereof. The term "nonvolatile oil" is understood as an oil that remains on a surface at room temperature (25° C.) and normal pressure (1 atm) for at least 2 hours and has in particular a vapor pressure lower than 10 mm Hg (0.13 Pa). A non-volatile oil may be defined as an oil having an evaporation rate such that, at room temperature (25° C.) and normal pressure (1 atm), the quantity evaporated at the end of 30 minutes is smaller than 0.07 mg/cm$^2$.

The term "volatile oil" is understood as an oil that is volatile at ambient temperature (25° C.) and normal pressure (1 atm) and for purposes of the instant disclosure may be an oil capable of evaporating on contact with the skin in less than one hour, at room temperature and atmospheric pressure. Volatile oils may be defined as oils having a non-zero vapor pressure at room temperature and atmospheric pressure, in particular having a vapor pressure of between 0.13 Pa and 40,000 Pa (0.001 to 300 mm of Hg), preferably between 1.3 Pa and 13,000 Pa (0.01 to 100 mm of Hg), and more preferably still between 1.3 Pa and 1,300 Pa (0.01 to 1000 mm of Hg). Preferred volatile oils include volatile hydrocarbon oils, volatile silicone oils, and combinations thereof.

Nonlimiting examples of oils include oils of plant origin, oils of animal original, synthetic oils, hydrocarbon oils, ester oils, silicone oils, fatty alcohols, and liquid triglycerides. Preferably, the hair treatment serum comprises one or more hydrocarbon oils and one or more silicone oils. More preferably, the hair treatment serum includes one or more hydrocarbon oils, one or more silicone oils, and one or more ester oils.

The total amount of the one or more oils in the hair treatment serum will vary but is typically from about 2 to about 15 wt. %, based on the total weight of the hair treatment serum. In further embodiments, the hair treatment serum includes from about 2 to about 12 wt. %, about 2 to about 10 wt. %, about 2 to about 8 wt. %, about 2 to about 7 wt. %, about 3 to about 15 wt. %, about 3 to about 12 wt. %, about 3 to about 10 wt. %, about 3 to about 8 wt. %, about 3 to about 7 wt. %, about 4 to about 15 wt. %, about 4 to about 12 wt. %, about 4 to about 10 wt. %, about 4 to about 8 wt. %, about 4 to about 7 wt. %, about 5 to about 15 wt. %, about 5 to about 12 wt. %, about 5 to about 12 wt. %, about 5 to about 10 wt. %, about 5 to about 8 wt. %, or about 5 to about 7 wt. % of the one or more oils, based on the total weight of the hair treatment serum. Preferably, the hair treatment serum includes from about 2 to about 15 wt. %, more preferably from about 5 to about 12 wt. %, and even more preferably from about 6 to about 10 wt. % of one or more oils, based on the total weight of the hair treatment serum.

As noted above, the one or more oils are part of the oil phase of the oil-in-water emulsion or oil-in-water dispersion. The oil phase may comprise, consist essentially of, or consist of the one or more oils. Nonetheless, the total amount of the oil phase is typically about 2 to about 15 wt. %, based on the total weight of the hair treatment serum. In further embodiments, the hair treatment serum includes from about 2 to about 12 wt. %, about 2 to about 10 wt. %, about 2 to about 8 wt. %, about 2 to about 7 wt. %, about 3 to about 15 wt. %, about 3 to about 12 wt. %, about 3 to about 10 wt. %, about 3 to about 8 wt. %, about 3 to about 7 wt. %, about 4 to about 15 wt. %, about 4 to about 12 wt. %, about 4 to about 10 wt. %, about 4 to about 8 wt. %, about 4 to about 7 wt. %, about 5 to about 15 wt. %, about 5 to about 12 wt. %, about 5 to about 12 wt. %, about 5 to about 10 wt. %, about 5 to about 8 wt. %, or about 5 to about 7 wt. % of the oil phase, based on the total weight of the hair treatment serum. Preferably, the hair treatment serum includes from about 2 to about 15 wt. %, more preferably from about 5 to about 12 wt. %, and even more preferably from about 6 to about 10 wt. % of the oil phase, based on the total weight of the hair treatment serum.

(b)(i) Hydrocarbon Oils

The term "hydrocarbon oil" is understood as an oil formed substantially, even constituted of carbon and hydrogen atoms, and possibly of oxygen, nitrogen atoms, and not containing silicon or fluorine atoms. It may contain alcohol ester, ether, carboxylic acid, amine and/or amide groups.

The hair treatment serum preferably includes one or more hydrocarbon oils. Nonlimiting examples of hydrocarbon oils include undecane, tridecane, tetradecane, pentadecane, hexadecane, octadecane, docosane, squalane, hydrogenated polyisobutene, polybutene, hydrogenated polydecene, hydrogenated didecene, mineral oil, liquid, petrolatum, dodecane, isododecane, isoeicosane, isohexadecane, isoparaffin, isodecanefarnesene, hydrogenated farnesene, coconut alkanes, coconut/palm kernel alkanes, C9-C12 alkane, C10-C13 alkane, alkane, C12-C17 alkane, C13-C15 alkane, C13-15 alkane, C13-14 alkane, C14-17 alkane, C14-19 alkane, C15-19 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C11-C16 isoalkane, C12-C20 isoalkane, C13-C14 isoalkane, C13-C16 isoalkane, C14-C16 isoalkane, C15-C19 isoalkane, or mixtures thereof.

The hair treatment serum may optionally include one or more volatile hydrocarbon oils. Nonlimiting examples of volatile hydrocarbon oils include linear or branched, optionally cyclic, C5-C20 lower alkanes, such as, pentane, hexane, heptane, decane, undecane, dodecane, tridecane, tetradecane, and C8-C18 isoparaffins, for example, isodecane, isododecane and isohexadecane.

In a preferred embodiment, the hair treatment serum includes one or more hydrocarbon oils selected from C13-15 alkane, hydrogenated polydecene, hydrogenated polyisobutene, isododecane, isohexadecane, squalane, undecane, tridecane, C13-14 alkane, C14-17 alkane, C14-19 alkane, C15-19 alkane, or mixtures thereof. In a preferred embodiment, the hair treatment serum includes one or more hydrocarbon oils selected from squalane, liquid paraffin, C12-15 alcohol benzoates, hydrogenated polyisobutene, and hydrogenated polydecene. Squalane is particularly preferred.

Preferably, the hair treatment serum includes one or more nonpolar hydrocarbon oils, which may be linear or branched, and contain at least 20 carbon atoms, such as paraffinic hydrocarbons and olefins, for example, C24-28 olefins, C30-45 olefins, C20-40 isoparaffins, hydrogenated polyisobutene, polyisobutene, polydecene, hydrogenated polydecene, mineral oil, petrolatum, pentahydrosqualene, squalene, and squalane. Preferably, the nonpolar hydrocarbon oils have a molecular weight ranging from about 300 to 1000 Daltons.

The total amount of the one or more hydrocarbon oils in the hair treatment serum will vary but is typically from about 0.1 to about 5 wt. %, based on the total weight of the hair treatment serum. In further embodiments, the hair treatment serum includes about 0.1 to about 4 wt. %, about 0.1 to about 3 wt. %, about 0.1 to about 2 wt. %, about 0.2 to about 5 wt. %, about 0.2 to about 4 wt. %, about 0.2 to about 3 wt. %, about 0.2 to about 2 wt. %, about 0.4 to about 5 wt. %, about 0.4 to about 4 wt. %, about 0.4 to about 3 wt. %, about 0.4 to about 2 wt. %, or about 0.4 to about 1 wt. % of one or more oils, based on the total weight of the hair treatment serum. Preferably, the hair treatment serum includes from about 0.1 to about 4 wt. %, more preferably from about 0.2 to about 4 wt. %, and even more preferably from about 0.2 to about 3 wt. % of one or more oils, based on the total weight of the hair treatment serum.

Weight Ratio of (a) to ((b)(i)

The amounts of the polyglutamic acid, salts thereof, or combination thereof of (a) and the one or more hydrocarbon oils of (b)(i) will vary. Nonetheless, the amount of the polyglutamic acid, salts thereof, or combination thereof of (a) and the amount of the one or more hydrocarbon oils of (b)(i) are typically in a weight ratio of about 1:1 to about 1:25 ((a):(b)(i)). In further embodiments, the weight ratio is about 1:1 to about 1:20, about 1:1 to about 1:15, about 1:1 to about 1:10, about 1:1 to about 1:8, about 1:1 to about 1:5, about 1:1 to about 1:3, about 1:2 to about 1:25, about 1:2 to about 1:20, about 1:2 to about 1:15, about 1:2 to about 1:10, about 1:2 to about 1:8, about 1:2 to about 1:5, or about 1:2 to about 1:3 ((a):(b)(i)). Preferably, the amount of the polyglutamic acid, salts thereof, or combination thereof of (a) and the amount of the one or more hydrocarbon oils of (b)(i) are in a weight ratio of about 1:1 to about 1:10, more preferably about 1:1 to about 1:5, and even more preferably about 1:2 to about 1:5 ((a):(b)(i)).

(b)(ii) Silicone Oils

The term "silicone oil" is understood as an oil comprising at least one silicon atom, and especially comprising Si—O groups and encompasses amino-functionalized silicone oils (also referred to as "amino silicones"). An "amino-functionalized silicone" is a polyaminosiloxane, i.e. any polysiloxane comprising at least one primary, secondary or tertiary amine function or a quaternary ammonium group.

Nonlimiting examples of silicones oils that are not amino-functionalized silicone oils include dimethicone, dimethiconol, cyclomethicone, polysilicone-11, phenyl trimethicone, and stearoxytrimethylsilane. Nonlimiting examples of amino-functionalized silicones include amodimethicone, bis-aminopropyl dimethicone, and trimethyl silylamodimethicone. Amodimethicone is a particularly preferred amino-functionalized silicone.

The one or more silicone oils may optionally include or be selected from volatile silicone oils. Nonlimiting examples of volatile silicone oils include hexamethylcyclo-trisiloxane, octamethylcyclotetrasiloxane, decamethylcyclopentasiloxane, dodecamethylcyclohexasiloxane, cyclotetradimethylsiloxane, cyclopentadimethylsiloxane, hoxilisilisilisethylsiloxane, xyamethylsiloxylistroxane, octamethylsiloxilhexylsiloxane, octamethylsilohexethylsiloxan octylheptamethyltrisiloxane, decamethyltetrasiloxane, dodecamethylpentasiloxane, heptamethylhexyl trisiloxane, and heptamethyloctyl trisiloxane.

The one or more silicones oils may include or be selected from nonvolatile silicon oils. For example, nonlimiting examples of useful nonvolatile silicone oils include polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl (methyldiphenyl)trisiloxanes or (2-phenylethyl)trimethylsiloxysilicates. Other examples of silicone oils that may be mentioned include volatile linear or cyclic silicones, such as those with a viscosity 8 centistokes (8×106 m2/s) and/or containing from 2 to 7 silicon atoms. These silicone oils optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or mixtures thereof.

Preferably, at least one of the one or more silicone oils is selected from nonvolatile silicone oils, in particular, nonvolatile, nonpolar silicone oils, for example, polyalkylsiloxanes, polyarylsiloxanes, polyalkylarylsiloxanes, and mixtures thereof. Methyl substituted polyorganosiloxanes are also known as polydimethylsiloxanes (PDMS) or dimethicone (INCI) is particularly preferred. Dimethicone is available in various chain lengths and with various molecular weights and is a preferred silicone oil.

In a preferred embodiment, the hair treatment serum includes one or more amino functionalized silicone oils. Nonlimiting examples of amino-functionalized silicone oils include amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. Amodimethicone is a particularly useful amino functionalized silicone.

In a preferred embodiment the one or more silicone oils are chosen from dimethicone, dimethiconol, cyclopentasiloxane, cyclomethicone, cyclotetrasiloxane, cyclohexasiloxane, cycloheptasiloxane, decamethylcyclopentasiloxane, cyclotetrasiloxane, cyclotrisiloxane, capryldimethicone, caprylyl trimethicone, caprylyl methicone, cetearylmethicone, hexadecylmethicone, hexylmethicone, lauryl methicone, myristyl methicone, phenyl methicone, stearyl methicone, stearyl dimethicone, behenyl dimethicone, trifluoropropyl methicone, cetyl dimethicone, polyphenylmethylsiloxane, dimethylpolysiloxane, methylphenylpolysiloxane, methyltrimethicone, diphenylsiloxyphenyl trimethicone, and phenyl trimethicone, and mixtures thereof.

In a preferred embodiment, the cosmetic compositions include one or more silicone oils chosen from dimethicone, dimethiconol, cyclomethicone, polysilicone-11, phenyl trimethicone, amodimethicone, or combinations thereof.

In a particularly preferred embodiment, the hair treatment serum includes:

(a) about 0.1 to about 5 wt. %, preferably about 0.2 to about 4 wt. %, more preferably about 0.5 to about 3 wt. % of one or more silicone oils selected from dimethicone, dimethiconol, cyclomethicone, polysilicone-11, phenyl trimethicone, or mixtures thereof, preferably one or more silicone oils selected from dimethicone, dimethiconol, cyclomethicone, phenyl trimethicone, or mixtures thereof, more preferably dimethicone, dimethiconol, or a mixture thereof; and (b) about 0.1 to about 5 wt. %, preferably about 0.2 to about 4 wt. %, more preferably about 0.5 to about 3 wt. % of one or more amino-functionalized silicones selected from amodimethicone, bis-hydroxy/methoxy amodimethicones, bis-cetearyl amodimethicone, bis (C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, or mixtures thereof, more preferably selected from amodimethicone, aminopropyl phenyl trimethicones, aminopropyl dimethicones, or mixtures thereof, even more preferably, amodoimethicone.

The total amount of the one or more silicone oils in the hair treatment serum will vary. Nonetheless, the hair treatment serum typically includes from about 0.1 to about 10 wt. % of one or more silicone oils. In further embodiments, the hair treatment serum includes about 0.1 to about 8 wt. %, about 0.1 to about 6 wt. %, about 0.1 to about 5 wt. %, about 0.1 to about 4 wt. %, about 0.5 to about 10 wt. %, about 0.5 to about 8 wt. %, about 0.5 to about 6 wt. %, about 0.5 to about 5 wt. %, about 0.5 to about 4 wt. %, about 1 to about 10 wt. %, about 1 to about 8 wt. %, about 1 to about 6 wt. %, about 1 to about 5 wt. %, about 1 to about 4 wt. %, about 2 to about 10 wt. %, about 2 to about 8 wt. %, about 2 to about 6 wt. %, about 2 to about 5 wt. %, or about 2 to about 4 wt. % of one or more silicone oils, based on the total weight of the hair treatment serum. Preferably, the hair treatment serum includes from about 0.1 to about 8 wt. %, more preferably about 0.5 to about 6 wt. %, even more preferably about 1 to about 5 wt. % of one or more silicone oils, based on the total weight of the hair treatment composition.

(b)(iii) Ester Oils

The term "ester oil" is understood as an oil having at least one ester function in its molecule. Nonlimiting examples of ester oils include cetyl ethylhexanoate, hexyldecyl ethylhexanoate, isocetyl myristate, isotridecyl isononanoate, pentaerythrityl tetraisostearate, pentaerythrityl tetraethylhexanoate, triethylhexanoin, caprylic/capric triglyceride, coco-caprylate/caprate, dicaprylyl carbonate, phytosteryl/octyldodecyl lauroyl glutamate, trimethylolpropane tricaprylate/tricaprate, dipentaerythrityl hexa C5-9 acid esters, diisostearyl malate, hexyl laurate, neopentyl glycol diheptanoate, ethyl isostearate, isopropyl myristate, isostearyl isostearate, octyldodecyl myristate, diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, octyldodecyl myristate, 2-hexyldecyl myristate, myristyl myristate, hexyldecyl dimethyloctanoate, ethyl laurate, hexyl laurate, diisostearyl malate, dicaprylyl carbonate, and mixtures thereof.

In a preferred embodiment, the one or more ester oils are selected from isopropyl myristate, isopropyl palmitate, isopropyl laurate, isopropyl lanolinate, isopropyl ricinoleate, isopropyl stearate, isononyl nonanoate, alkyl benzoate, dicaprylyl carbonate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, or mixtures thereof. Isopropyl myristate is a particularly preferred ester oil.

The total amount of the one or more ester oils in the hair treatment serum will vary. Nonetheless, the hair treatment serum typically includes from about 1 to about 15 wt. % of one or more ester oils, based on the total weight of the hair treatment serum. In further embodiments, the hair treatment serum includes about 1 to about 12 wt. %, about 1 to about 10 wt. %, about 1 to about 8 wt. %, about 1 to about 5 wt. %, about 2 to about 15 wt. %, about 2 to about 12 wt. %, about 2 to about 10 wt. %, about 2 to about 8 wt. %, about 2 to about 5 wt. %, about 3 to about 15 wt. %, about 3 to about 12 wt. %, about 3 to about 10 wt. %, about 3 to about 8 wt. %, about 3 to about 5 wt. %, or about 3 to about 4 wt. % of one or more ester oils, based on the total weight of the hair treatment serum. Preferably, the hair treatment serum includes from about 1 to about 10 wt. %, more preferably from about 2 to about 8 wt. %, and even more preferably about 2 to about 5 wt. % of one or more ester oils, based on the total weight of the hair treatment serum.

(b)(iv) Fatty Alcohols

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, comprising from 8 to 40 carbon atoms, preferably 10 to 30 carbon atoms, more preferably 12 to 24 carbon atoms, and even more preferably 14 to 22 carbon atoms.

The hair treatment serum optionally includes one or more fatty alcohols. In certain embodiments, the hair treatment serum includes one or more oils and at least one of the one or more oils is a fatty alcohol. However, in other embodiments, the hair treatment serum is free or essentially free from fatty alcohols.

Fatty alcohol(s) may be liquid or solid. The liquid fatty alcohols, in particular those containing C10-C34, preferably have branched carbon chains and/or have one or more, preferably 1 to 3 double bonds. They are preferably branched and/or unsaturated (C═C double bond) and contain from 12 to 40 carbon atoms.

The liquid fatty alcohols may be represented by: R—OH, wherein R denotes a C12-C24 branched alkyl group or an alkenyl group (comprising at least one C12-C24 double bond C═C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

Solid fatty alcohols are solid at ambient temperature and at atmospheric pressure (25° C., 780 mmHg), and are insoluble in water, that is to say they have a water solubility of less than 1% by weight, preferably less than 0.5% by weight, at 25° C., 1 atm. The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Nonlimiting examples of fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol), and mixtures thereof. In various embodiments, the hair treatment serum includes one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof.

The total amount of the one or more fatty alcohols in the hair treatment serum, if present, will vary. Nonetheless, in various embodiments, the hair treatment serum includes from about 0.01 to about 5 wt. % of one or more fatty alcohols. In further embodiments, the hair treatment serum includes from about 0.01 to about 3 wt. %, about 0.01 to about 2 wt. %, about 0.05 to about 5 wt. %, about 0.05 to about 3 wt. %, about 0.05 to about 2 wt. %, about 0.1 to about 5 wt. %, about 0.1 to about 3 wt. %, about 0.1 to about 2 wt. %, about 0.5 to about 5 wt. %, about 0.5 to about 3 wt. %, about 0.5 to about 2 wt. %, about 1 to about 5 wt. %, or about 1 to about 3 wt. % of one or more fatty alcohols based on the total weight of the hair treatment serum. If present, the hair treatment serum preferably includes from about 0.01 to about 5 wt. %, more preferably about 0.05 to about 4 wt. %, and more preferably from about 0.1 to about 3 wt. % of one or more fatty alcohols, based on the total weight of the hair treatment serum. In a particularly preferred embodiment, the hair treatment serum is free or essentially free from fatty alcohols.

(c) Thickening Agents

The term "thickening agent" may interchangeably be referred to as "thickener" or "viscosity modifying agent." Thickening agents include, but are not limited to, polymer thickening agents (or thickening polymers), mineral thickening agents, aqueous thickening agents, non-aqueous thickening agents, and combinations thereof. Nonlimiting examples of aqueous thickening agents include cellulose, cellulose derivatives, guar gum, guar derivatives, xanthan gum, xanthan derivatives, carbomers, acrylate/VA crosspolymers, polyethylene glycols, and clays. Nonlimiting examples of non-aqueous thickening agents include polyethylenes, trihydroxstearin, organoclays, and fumed silica.

Nonlimiting examples of polymer thickening agents (or thickening polymers) include: (a) vinylpyrrolidone and copolymers of vinylpyrrolidone such as vinylpyrrolidone/hexadecene copolymer and vinylpyrrolidone/eicosene copolymer; (b) acrylates, methacylates, and copolymers thereof, for example, copolymers of $C_1$-$C_6$ alkyl methacrylates or acrylates and of amphiphilic monomers comprising at least one fatty chain, for instance the oxyethylenated methyl acrylate/stearyl acrylate copolymer; (c) copolymers of hydrophilic methacrylates or acrylates and of hydrophobic monomers comprising at least one fatty chain, for instance the polyethylene glycol methacrylate/lauryl methacrylate copolymer; (d) polyurethanes and polyurethane polyethers, for example polyurethane polyethers comprising in their chain both hydrophilic blocks usually of polyoxyethylenated nature and hydrophobic blocks, which may be aliphatic sequences alone and/or cycloaliphatic and/or aromatic sequences; (e) taurate copolymers, for example, acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, and hydroxyethyl acrylate/sodium acryloyldimethyl taurate copolymer; (f) polyacrylic acid thickening agents including crosslinked polyacrylic acid thickening agents and copolymers of acrylic acid; and (g) polysaccharide thickening agents, including gums and derivatives thereof.

Preferably, the hair treatment serum includes one or more polyacrylic acid thickening agents, especially crosslinked polyacrylic acid thickening agents such as carbomers. More preferably, the hair treatment serum includes one or more polyacrylic acid thickening agents and one or more polysaccharide thickening agents.

The total amount of the one or more thickening agents in the hair treatment serum will vary. Nonetheless, the hair treatment serum typically includes from about 0.1 to about 8 wt. % of one or more thickening agents, based on the total weight of the hair treatment serum. In further embodiments, the hair treatment serum includes about 0.1 to about 5 wt. %, about 0.1 to about 4 wt. %, about 0.1 to about 3 wt. %, about 0.1 to about 2 wt. %, about 0.2 to about 8 wt. %, about 0.2 to about 5 wt. %, about 0.2 to about 4 wt. %, about 0.2 to about 3 wt. %, about 0.2 to about 2 wt. %, about 0.5 to about 8 wt. %, about 0.5 to about 5 wt. %, about 0.5 to about 4 wt. %, about 0.5 to about 3 wt. %, about 0.5 to about 2 wt. %, about 1 to about 8 wt. %, about 1 to about 5 wt. %, about 1 to about 4 wt. %, about 1 to about 3 wt. %, about 1 to about 3 wt. %, or about 1 to about 2 wt. %, based on the total weight of the hair treatment serum. Preferably, the hair treatment serum includes from about 0.1 to about 5 wt. %, more preferably from about 0.2 to about 4 wt. %, and even more preferably from about 0.5 to about 3 wt. % of one or more thickening agents, based on the total weight of the hair treatment serum.

(c)(i) Polyacrylic Acid Thickening Agents

As used herein, a "polyacrylic acid thickening agent" refers to water soluble homopolymers of acrylic acid or methacrylic acid or water-dispersible or water-soluble salts, esters, and amides thereof, or water-soluble copolymers of these acids or their salts, esters, or amides with each other or with one or more ethylenically unsaturated monomers, such as styrene, maleic acid, maleic anhydride, 2-hydroxyethylacrylate, acrylonitrile, vinyl acetate, ethylene, propylene, or the like. The polyacrylic acid thickening agents include acrylic acid homopolymers and copolymers comprising 90% or more, by weight, polymerized acrylic acid units. The preferred acrylic acid monomer used to make these thickeners is the actual compound "acrylic acid." However, other acrylic acids can also be employed, e.g., methacrylic acid and C1-4 alkyl substituted acrylic acid. Other comonomers that may be present in the polymer chain include 10% by weight or less long chain alkyl esters of acrylic acid. Further, the term "polyacrylic acid thickening agents" encompasses salts of the polyacrylic acid, e.g., sodium polyacrylate, potassium polyacrylate, etc.

Examples of the polyacrylic acid thickening agents include polyacrylic acid (homopolymer of acrylic acid), sodium polyacrylate, and ammonium polyacrylate. Examples of a commercially available product of the polyacrylic acid thickener include "ARON A-10H" (polyacrylic acid), "ARON A-20L" (sodium polyacrylate), "ARON A-7100" (sodium polyacrylate), "ARON A-30" (ammonium polyacrylate), and "ARON A-7195" (ammonium polyacrylate) manufactured by TOAGOSEI CO., LTD, and preferably, "ARON A-10H" is used. These polyacrylic acid thickeners may be used alone or in combination of two or more.

Suitable thickeners include the crosslinked polyacrylic acid products sold under the tradenames CARBOPOL®1342, Carbopol®. 1382, Carbopol® ETD 2020, Carbopol® Ultrez™ 10, Carbopol®940, Carbopol EZ-1™, Carbopol EZ-2™, and Carbopol EZ-ultra™ and Carbopol®980 y. The USP-NF, British Pharmacopoeia, United States Adopted Names Council (USAN), and Cosmetic, Toiletries and Fragrance Association (CTFA) have adopted the generic (i.e. non-proprietary) name "carbomer" for the Carbopol® homopolymers. The Japanese Pharmaceutical Excipients list Carbopol® homopolymers as "carboxyvinyl polymer" and "carboxy polymethylene." The polymers share an acrylic acid backbone. The main differences relate to the presence of comonomer and crosslink density. These polymers are either homopolymers of acrylic acid cross-linked with allyl sucrose, polyalkyl ethers of divinyl glycol, or allyl pentaerythritol or similarly crosslinked copolymers of acrylic acid with minor levels of long chain alkyl acrylate comonomers. These polymers swell in water up to 1000 times their original volume (and ten times their original diameter) to form a gel when exposed to a pH environment above 4.0-6.0.

In a preferred embodiment, the hair treatment serum includes one or more polyacrylic acid homopolymers, preferably crosslinked, known as carbomers.

The total amount of the one or more polyacrylic acid thickening agents in the hair treatment serum will vary. Nonetheless, the hair treatment serum typically includes from about 0.1 to about 5 wt. % of one or more polyacrylic acid thickening agents, based on the total weight of the hair treatment serum. In further embodiments, the hair treatment serum includes about 0.1 to about 4 wt. %, about 0.1 to about 3 wt. %, about 0.1 to about 2 wt. %, about 0.1 to about 1 wt. %, about 0.2 to about 5 wt. %, about 0.2 to about 4 wt. %, about 0.2 to about 3 wt. %, about 0.2 to about 2 wt. %, about 0.2 to about 1 wt. %, about 0.5 to about 5 wt. %, about 0.5 to about 4 wt. %, about 0.5 to about 3 wt. %, about 0.5 to about 2 wt. %, or about 0.5 to about 1 wt. % of one or more polyacrylic acid thickening agents, based on the total weight of the hair treatment serum. Preferably, the hair treatment serum includes from about 0.1 to about 5 wt. %, more preferably from about 0.2 to about 4 wt. %, and even more preferably about 0.2 to about 3 wt. % of one or more polyacrylic acid thickening agents, based on the total weight of the hair treatment serum.

Weight Ratio of (a) to ((c)(i)

The amounts of the polyglutamic acid, salts thereof, or combination thereof of (a) and the one or more a polyacrylic acid thickening agent of (c)(i) will vary. Nonetheless, the amount of the polyglutamic acid, salts thereof, or combination thereof of (a) and the amount of the one or more a polyacrylic acid thickening agent of (c)(i) are typically in a weight ratio of about 1:1 to about 1:25 ((a):(c)(i)). In further embodiments, the weight ratio is about 1:1 to about 1:20, about 1:1 to about 1:15, about 1:1 to about 1:10, about 1:1 to about 1:8, about 1:1 to about 1:5, about 1:1 to about 1:3, about 1:2 to about 1:25, about 1:2 to about 1:20, about 1:2 to about 1:15, about 1:2 to about 1:10, about 1:2 to about 1:8, about 1:2 to about 1:5, or about 1:2 to about 1:3 ((a):(c)(i)). Preferably, the amount of the polyglutamic acid, salts thereof, or combination thereof of (a) and the amount of the one or more a polyacrylic acid thickening agent of (c)(i) are in a weight ratio of about 1:1 to about 1:10, more preferably about 1:1 to about 1:5, and even more preferably about 1:2 to about 1:5 ((a):(c)(i)).

(c)(ii) Polysaccharide Thickening Agents

In various preferred embodiments, the one or more thickening agent includes or consists of one or more polysaccharide thickening agents. The term "polysaccharides" refers to compounds containing a backbone of repeating sugar (i.e., carbohydrate) units. As the name suggests, a "polysaccharide thickening agent" is an agent that increases the viscosity (thickness) of a composition. The polysaccharide thickening agents may be cationic, nonionic, or anionic. In various embodiments, the polysaccharide thickening agent is preferably a nonionic polysaccharide thickening agents, a cationic thickening agents, or combinations thereof. In another preferred embodiment, the hair treatment serum includes one or more nonionic polysaccharide thickening agents. Nonlimiting examples of polysaccharide thickening agents include inulins, inulin derivatives, celluloses, cellulose derivatives, starches, starch derivatives, guar gums, guar derivatives, xanthan gums, xanthan derivatives, pullulan gums, pullulan derivatives alginate gums, alginate derivatives, agar-agar gums, agar derivatives, carrageenan gums, carrageneenan derivatives, gellan gums, gellan derivatives, gum Arabics, and gum Arabic derivatives, xyloses, xylose derivatives tragacanth gums, tragacanth derivatives, and combinations thereof. More specific but nonlimiting examples of polysaccharide thickening agents include guar gum, hydroxpropyl guar, starch, modified starch, maltodextrin, scleroglucan, pectin, chitosan, and mixtures thereof.

Non-limiting examples of gums include acacia, agar, algin, alginic acid, ammonium alginate, amylopectin, calcium alginate, calcium carrageenan, carnitine, carrageenan, dextrin, gelatin, gellan gum, guar gum, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, dehydroxanthan gum, and biosaccharide gum. Modified gums or derivatives of gums may also be used, such as, for example, deacylated gellan gum, welan gum, or hydroxypropylated guar gum, or mixtures thereof. In various embodiments, the one or more polysaccharide thickening agents are selected from gums, such as gum arabic, tragacanth gum, karaya gum, guar gum, hydroxypropyl guar, gellan gum, tara gum, locust bean gum, tamarind gum, xanthan gum, dehydroxanthan gum, Seneca gum, *sclerotium* gum, gellan gum, or mixtures thereof.

Nonlimiting examples of celluloses and cellulose derivatives include methyl cellulose, hydroxyalkylcelluloses, such as hydroxymethylcellulose, methylhydroxyethylcellulose, hydroxyethylcelluloses, hydroxypropylmethylcellulose, hydroxybutylcellulose, hydroxyethylmethylcellulose (also known as methyl hydroxyethylcellulose) or hydropropylcelluloses, which may or may not contain a fatty chain. One particularly suitable hydroxypropylmethylcellulose is METHOCEL® F4M sold by Dow Chemicals (INCI name: hydroxypropylmethylcellulose). Celluloses modified with groups comprising one or more nonionic fatty chains that can be used include hydroxyethylcelluloses, preferably nonionic hydroxyethylcelluloses, modified by groups comprising at least one fatty chain, such as alkyl, arylalkyl or alkylaryl groups, or their mixtures, and in which the alkyl groups are preferably C8-C22 alkyl groups, such as the product NATROSOL™ PLUS GRADE 330 CS (C16 alkyls), sold by Aqualon, corresponding to the INCI name cetylhydroxyethylcellulose, or the product BERMOCOLL® EHM 100 sold by Berol Nobel, and those modified with alkylphenyl polyalkylene glycol ether groups, such as the product AMERCELL POLYMER®HM-1500 (nonylphenyl polyethylene glycol (15) ether) sold by Amerchol that corresponds to the INCI name nonoxynyl hydroxyethylcellulose. Nonlimiting examples of celluloses (also called "cellulose-based polymers") include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

Also, useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename NATROSOL® CS Plus from Aqualon Corporation.

Nonlimiting examples of guar gum and guar derivatives include guar gum, hydroxypropyl guar, guar hydroxypropyltrimonium chloride, hydroxypropyl guar hydroxypropyltrimonium chloride, and mixtures thereof. Additional examples include hydroxypropyl guars modified with groups comprising at least one fatty chain, such as the product ESAFLOR® HM 22 (C22 alkyl chain) sold by the company Lamberti, and the products RE210-18™ (C14 alkyl chain) and RE205-1™ (C20 alkyl chain) sold by the company Rhone-Poulenc. The total amount of the guar gum, guar derivatives, or mixtures thereof, if present, is typically from about 0.1 to about 3 wt. %, based on the total weight of the hair treatment serum. More preferably, however, the hair treatment serum includes about 0.1 to about 2 wt. % even more preferably from about 0.2 to about 1 wt. % of one or more guar gums, guar derivatives, or mixtures thereof.

Nonlimiting examples of starches include modified starches, starch-based polymers, methylhydroxypropyl starch, potato starch, modified potato starch, wheat starch, rice starch, starch crosslinked with octenyl succinic anhydride, starch oxide, dialdehyde starch, dextrin, British gum, acetyl starch, starch phosphate, carboxymethyl starch, hydroxyethyl starch, hydroxypropyl starch, and mixtures thereof. The total amount of the one or more starches, derivatives of starches including modified starches, and mixtures thereof, if present, is typically from about 0.1 to about 3 wt. %, based on the total weight of the hair treatment serum. More preferably, however, the hair treatment serum includes about 0.1 to about 2 wt. % even more preferably from about 0.2 to about 1 wt. % of one or more starches, derivatives of starches including modified starches, and mixtures thereof.

In a preferred embodiment, the hair treatment serum includes one or more polysaccharide thickening agents selected from celluloses, cellulose derivatives, guar gum, guar derivatives, starch, modified starch, and derivatives of starch, and more preferably selected from guar gum, guar derivatives, starch, modified starch, starch derivatives, and mixtures thereof. Preferred guar derivatives include hydroxypropyl guar, guar hydroxypropyltrimonium chloride, hydroxypropyl guar hydroxypropyltrimonium chloride, and mixtures thereof. Preferred starches include modified starches, starch-based polymers, methylhydroxypropyl starch, potato starch, wheat starch, rice starch, starch crosslinked with octenyl succinic anhydride starch oxide, dialdehyde starch, dextrin, British gum, acetyl starch, starch phosphate, carboxymethyl starch, hydroxyethyl starch, hydroxypropyl starch, and mixtures thereof.

The total amount of the one or more polysaccharide thickening agents in the hair treatment serum will vary. Nonetheless, the hair treatment serum typically includes from about 0.1 to about 5 wt. % of one or more polysaccharide thickening agents, based on the total weight of the hair treatment serum. In further embodiments, the hair treatment serum includes about 0.1 to about 4 wt. %, about 0.1 to about 3 wt. %, about 0.1 to about 2 wt. %, about 0.1 to about 1 wt. %, about 0.2 to about 5 wt. %, about 0.2 to about 4 wt. %, about 0.2 to about 3 wt. %, about 0.2 to about 2 wt. %, about 0.2 to about 1 wt. %, about 0.5 to about 5 wt. %, about 0.5 to about 4 wt. %, about 0.5 to about 3 wt. %, about 0.5 to about 2 wt. %, or about 0.5 to about 1 wt. % of one or more polysaccharide thickening agents, based on the total weight of the hair treatment serum. Preferably, the hair treatment serum includes from about 0.1 to about 5 wt. %, more preferably from about 0.2 to about 4 wt. %, and even more preferably about 0.2 to about 3 wt. % of one or more polysaccharide thickening agents, based on the total weight of the hair treatment serum.

(c)(iii) Additional Thickening Agents

Other than the one or more polyacrylic acid thickening agents and the one or more polysaccharide thickening agents set forth above, the hair treatment serum may optionally include one or more additional thickening agents, including the thickening agents sets forth above that differ from the polyacrylic acid thickening agents and the polysaccharide thickening agents. Nonlimiting examples of additional thickening agents include thickening polymers selected from taurate copolymer, polyacrylamide, acrylic acid/acrylonitrogens copolymer, acrylates/steareth-20 itaconate copolymer, acrylates/ceteth-20 itaconate copolymer, acrylates/aminoacrylates/C10-30 alkyl PEG-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, acrylates/palmeth-25 Acrylate copolymer, acrylic acid/acrylamidomethyl propane sulfonic Acid copolymer, and acrylates/C10-C30 alkyl acrylate crosspolymer, carbomers, hydrophobically modified polypolyacrylates; hydrophobically modified polyacrylic acids, hydrophobically modified polyacrylamides; hydrophobically modified polyethers wherein these materials may have a hydrophobe that can be selected from cetyl, stearyl, oleayl, and combinations thereof, acrylamide/ammonium acrylate copolymer, acrylates copolymer, acrylates crosspolymer-4, acrylates crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37, sodium polyacrylate, and a mixture thereof.

Nonlimiting examples of mineral thickening agents include silica silylate, fumed silica, zeolite, natural clay, synthetic clay, kaolin, hectorite, organically modified hectorite, pentaerythrityl tetraisostearate (and) disteardimonium hectorite (and) propylene carbonate, an activated clay, disteardimonium hectorite, stearalkonium hectorite, quaternium-18 bentonite, quaternium-18 hectorite, benzalkonium bentonite, and a mixture thereof.

Nonlimiting examples of taurate copolymers include acrylamide/sodium acryloyl dimethyl taurate copolymer, hydroxyethyl acrylate/sodium acryloyl dimethyl taurate copolymer, ammonium acryloyldimethyl taurate/VP copolymer, and mixtures thereof.

The total amount of the one or more additional thickening agents in the hair treatment serum, if present, will vary. Nonetheless, the hair treatment serum typically includes from about 0.1 to about 5 wt. % of one or more polysaccharide thickening agents, based on the total weight of the hair treatment serum. In further embodiments, the hair treatment serum includes about 0.1 to about 4 wt. %, about 0.1 to about 3 wt. %, about 0.1 to about 2 wt. %, about 0.1 to about 1 wt. %, about 0.2 to about 5 wt. %, about 0.2 to about 4 wt. %, about 0.2 to about 3 wt. %, about 0.2 to about 2 wt. %, about 0.2 to about 1 wt. %, about 0.5 to about 5 wt. %, about 0.5 to about 4 wt. %, about 0.5 to about 3 wt. %, about 0.5 to about 2 wt. %, or about 0.5 to about 1 wt. % of one or more additional thickening agents, based on the total weight of the hair treatment serum. Preferably, the hair treatment serum includes from about 0.1 to about 5 wt. %, more preferably from about 0.2 to about 4 wt. %, and even more preferably about 0.2 to about 3 wt. % of one or more additional thickening agents, based on the total weight of the hair treatment serum.

(d) Water and Water Phase

The total amount of water in the hair treatment serum will vary but is typically from about 60 to about 95 wt. %, based on the total weight of the hair treatment serum. In further embodiments, the hair treatment serum includes about 65 to about 95 wt. %, about 70 to about 95 wt. %, about 75 to about 95 wt. %, about 80 to about 95 wt. %, about 60 to about 92 wt. %, about 65 to about 92 wt. %, about 70 to about 92 wt. %, about 75 to about 92 wt. %, about 80 to about 92 wt. %, about 60 to about 90 wt. %, about 65 to about 90 wt. %, about 70 to about 90 wt. %, about 75 to about 90 wt. %, about 80 to about 90 wt. % of water, based on the total weight of the hair treatment serum. Preferably, the hair treatment serum includes from about 70 to about 95 wt. %, more preferably from about 75 to about 92 wt. %, and even more preferably from about 80 to about 90 wt. % of water, based on the total weight of the hair treatment serum.

As mentioned earlier, the hair treatment serum is typically an oil-in-water emulsion or oil-in-water dispersion. Accordingly, the hair treatment serum includes an aqueous phase (also referred to as a "water phase") and an oil phase (also referred to as a "fatty phase," "lipophilic phase," or "hydrophobic phase"). The aqueous phase includes water and ingredients that are soluble in water, such as water-soluble solvents, aqueous thickening agents, salts, acids, water-soluble active agents, and the like.

The total amount of aqueous phase in the hair treatment serum will vary but is typically from about 60 to about 95 wt. %, based on the total weight of the hair treatment serum. In further embodiments, the hair treatment serum includes about 65 to about 95 wt. %, about 70 to about 95 wt. %, about 75 to about 95 wt. %, about 80 to about 95 wt. %, about 60 to about 92 wt. %, about 65 to about 92 wt. %, about 70 to about 92 wt. %, about 75 to about 92 wt. %, about 80 to about 92 wt. %, about 60 to about 90 wt. %, about 65 to about 90 wt. %, about 70 to about 90 wt. %, about 75 to about 90 wt. %, about 80 to about 90 wt. % of the aqueous phase, based on the total weight of the hair treatment serum. Preferably, the hair treatment serum includes from about 70 to about 95 wt. %, more preferably from about 75 to about 92 wt. %, and even more preferably from about 80 to about 90 wt. % of an aqueous phase, based on the total weight of the hair treatment serum.

Ratio of Oil Phase to Water Phase

The ratio of oil phase to water phase will vary. Nonetheless, the aqueous phase of the hair treatment serum is typically larger than the oil phase. For example, the weight ratio of the oil phase to the aqueous phase is from about 1:2 to about 1:20 ((oil phase):(aqueous phase). In further embodiments, the weight ratio of the oil phase is from about 1:4 to about 20:1, about 1:5 to about 1:20, about 1:10 to about 1:20, about 1:4 to about 1:16, about 1:6 to about 1:16, about 1:8 to about 1:16, about 1:10 to about 1:16, about 1:5 to about 1:15, about 1:8 to about 1:15, or about 1:10 to about 1:15 ((oil phase):(aqueous phase). Preferably the weight ratio of the oil phase to the aqueous phase is from about 1:2 to about 1:20, more preferably from about 1:5 to about 1:16, and even more preferably from about 1:10 to 1:15 ((oil phase):(aqueous phase).

(e) Surfactants

The hair treatment serum typically includes one or more surfactants. The term "surfactants" is intended to also cover "emulsifiers." Surfactants include nonionic surfactants, amphoteric surfactants, anionic surfactants, and cationic surfactants. One or more nonionic surfactants are useful for emulsifying the oil-in-water emulsion or oil-in-water dispersion. Accordingly, in a preferred embodiment, the hair treatment serum includes one or more nonionic surfactants. Cationic surfactants can be helpful for emulsification but also provide conditioning properties to hair. Therefore, in a preferred embodiment, the hair treatment serum includes one or more cationic surfactants. In a particularly preferred embodiment, the hair treatment serum includes one or more nonionic surfactants and one or more cationic surfactants, and optionally, one or more amphoteric surfactants. The hair treatment serum is preferably free or essentially free from anionic surfactants.

The total amount of the one or more surfactants in the hair treatment serum will vary but is typically from about 0.05 to about 8 wt. %, based on the total weight of the hair treatment serum. In further embodiments, the hair treatment serum includes about 0.05 to about 5 wt. %, about 0.05 to about 4 wt. %, about 0.05 to about 3 wt. %, about 0.05 to about 2 wt. %, about 0.05 to about 1 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.5 to about 5 wt. %, about 0.5 to about 4 wt. %, about 0.5 to about 3 wt. %, or about 0.5 to about 2 wt. %, based on the total weight of the hair treatment serum.

(e)(i) Nonionic Surfactants

Nonlimiting examples of nonionic surfactants include those selected from alkyl polyglucosides; alcohols, alpha-diols, alkylphenols and esters of fatty acids, being ethoxylated, propoxylated or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof.

Nonionic surfactants include those of the alkyl(poly) glycoside type, represented especially by the following general formula: $R_1O—(R_2O)_t-(G)_v$ in which: $R_1$ represents a linear or branched alkyl or alkenyl substituent comprising 6 to 24 carbon atoms and especially 8 to 18 carbon atoms, or an alkylphenyl substituent whose linear or branched alkyl substituent comprises 6 to 24 carbon atoms and especially 8 to 18 carbon atoms; $R_2$ represents an alkylene substituent comprising 2 to 4 carbon atoms; G represents a sugar unit comprising 5 to 6 carbon atoms; t denotes a value ranging from 0 to 10 and preferably 0 to 4; and v denotes a value ranging from 1 to 15 and preferably 1 to 4. Preferably, the alkyl(poly)glycoside surfactants are compounds of the formula described above in which: $R_1$ denotes a linear or branched, saturated or unsaturated alkyl substituent comprising from 8 to 18 carbon atoms; $R_2$ represents an alkylene substituent comprising 2 to 4 carbon atoms; t denotes a value ranging from 0 to 3 and preferably equal to 0; and G denotes glucose, fructose or galactose, preferably glucose; the degree of polymerization, i.e. the value of v, possibly ranging from 1 to 15 and preferably from 1 to 4; the mean degree of polymerization more particularly being between 1 and 2. The glucoside bonds between the sugar units are generally of 1-6 or 1-4 type and preferably of 1-4 type. In particular, the alkyl(poly)glycoside surfactant may be an alkyl(poly)glucoside surfactant C8/C16 alkyl(poly)glucosides 1,4, and in particular decyl glucosides and caprylyl/capryl glucosides.

Nonionic surfactants include polyoxyethylenated C8-C30 fatty acid esters (preferably C12-C18) of sorbitan, polyethoxylated C8-C30 (preferably C12-18) fatty alcohols, polyglycerolated C8-C30 (preferably C12-C18) fatty acid esters, polyoxyethylenated compounds having preferably from 2 to 30 moles of ethylene oxide, polyglycerolated compounds having preferably from 2 to 16 moles of glycerol; and mixtures thereof. The polyoxyethylenated C8-C30 fatty alcohols may be chosen from C12-C18 fatty alcohols, in particular polyoxyethylenated lauryl alcohol, cetyl alcohol, myristyl alcohol, and stearyl alcohol having from 2 to 30 mol of ethylene oxide, such as: cetyl alcohol polyoxyethylenated with 2 EO (Ceteth-2) (HLB 5.3) cetyl alcohol polyoxyethylenated with 6 EO (Ceteth-6) (HLB 11.1) cetyl alcohol polyoxyethylenated with 10 EO (Ceteth-10) (HLB 12.9) cetyl alcohol polyoxyethylenated with 20 EO (Ceteth-20) (HLB 15.7) cetyl alcohol polyoxyethylenated with 24 EO (Ceteth-24) (HLB 16.3) lauryl alcohol polyoxyethylenated with 2 EO (laureth-2) (HLB 6.1) lauryl alcohol polyoxyethylenated with 3 EO (laureth-3) (HLB 8) lauryl alcohol polyoxyethylenated with 4 EO (laureth-4) (HLB 9.4) lauryl alcohol polyoxyethylenated with 7 EO (laureth-7) (HLB 12.3) lauryl alcohol polyoxyethylenated with 9 EO (laureth-9) (HLB 13.6) lauryl alcohol polyoxyethylenated with 10 EO (laureth-10) (HLB 13.9) lauryl alcohol polyoxyethylenated with 12 EO (laureth-12) (HLB 14.6) lauryl alcohol polyoxyethylenated with 21 EO (laureth-21) (HLB 15.5) lauryl alcohol polyoxyethylenated with 23 EO (laureth-23) (HLB 16.3) stearyl alcohol polyoxyethylenated with 2 EO (Steareth-2) (HLB 4.9) stearyl alcohol polyoxyethylenated with 10 EO (Steareth-10) (HLB 12.4) stearyl alcohol polyoxyethylenated with 20 EO (Steareth-20) (HLB 15.2) stearyl alcohol polyoxyethylenated with 21 EO (Steareth-21) (HLB 15.5).

The polyoxyethylenated C8-C30 fatty acid esters (preferably C12-C18) of sorbitan may be chosen from polyoxyethylenated esters of C12-C18 fatty acids, in particular lauric, myristic, cetylic or stearic acids, of sorbitan especially containing from 2 to 30 mol of ethylene oxide, such as: polyoxyethylenated sorbitan monolaurate (4 EO) (Polysorbate-21) (HLB 13.3) polyoxyethylenated sorbitan monolaurate (20 EO) (Polysorbate-20) (HLB 16.7) polyoxyethylenated sorbitan monopalmitate (20 EO) (Polysorbate-40) (HLB 15.6) polyoxyethylenated sorbitan monostearate (20 EO) (Polysorbate-60) (HLB 14.9) polyoxyethylenated sorbitan monostearate (4 EO) (Polysorbate-61) (HLB 9.6) polyoxyethylenated sorbitan monooleate (20 EO) (Polysorbate-80) (HLB 15). In a preferred embodiment, the hair treatment compositions include one or more nonionic surfactants chosen from polyoxyethylenated C8-C30 fatty acid esters (preferably C12-C18) of sorbitan, preferably polyoxyethylenated esters of C12-C18 fatty acids.

The polyglycerolated C8-C30 fatty acid esters, which are particularly preferred, may be chosen from polyglycerolated esters of C12-C18 fatty acids, in particular lauric, myristic, palmitic, stearic or isostearic acid, having from 2 to 16 mol of glycerol, such as: polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a C8-C24, preferably C12-C22, fatty acid or acids and alkoxylated derivatives thereof, preferably with a number of alkyleneoxide of from 10 to 200, and more preferably from 10 to 100; polyethylene glycol esters of a C8-C24, preferably C12-C22, fatty acid or acids and alkoxylated derivatives thereof, preferably with a number of alkyleneoxide of from 10 to 200, and more preferably from 10 to 100; sorbitol esters of a C8-C24, preferably C12-C22, fatty acid or acids and alkoxylated derivatives thereof, preferably with a number of alkyleneoxide of from 10 to 200, and more preferably from 10 to 100; sugar (sucrose, glucose, alkylglycose) esters of a C8-C24, preferably C12-C22, fatty acid or acids and alkoxylated derivatives thereof, preferably with a number of alkyleneoxide of from 10 to 200, and more preferably from 10 to 100; ethers of fatty alcohols; ethers of sugar and a C8-C24, preferably C12-C22, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids mention is made of glyceryl stearate (glyceryl monostearate, distearate, and/or tristearate) (CTFA name: glyceryl stearate) or glyceryl ricinoleate and mixtures thereof. As glyceryl esters of C8-C24 alkoxylated fatty acids, polyethoxylated glyceryl stearate (glyceryl mono-, di- and/or tristearate) such as PEG-20 glyceryl stearate can for example be cited Nonlimiting examples of alkyl polyglucosides include lauryl glucoside, octyl glucoside, decyl glucoside, coca glucoside, sucrose laurate, caprylyl/capryl glucoside, and sodium lauryl glucose carboxylate, and mixtures thereof.

Suitable alkoxylated monoacid surfactants include, but are not limited to: butoxynol-5 carboxylic acid, butoxynol-19 carboxylic acid, capryleth-4 carboxylic acid, capryleth-6 carboxylic Acid, capryleth-9 carboxylic acid, ceteareth-25 carboxylic acid, coceth-7 carboxylic acid, C9-11 pareth-6 carboxylic acid, C11-15 pareth-7 carboxylic acid, C12-13 pareth-5 carboxylic acid, C12-13 pareth-8 carboxylic acid, C12-13 pareth-12 carboxylic acid, C12-15 pareth-7 carboxylic acid, C12-15 pareth-8 carboxylic acid, C14-15 pareth-8 carboxylic acid, deceth-7 carboxylic acid, laureth-3 carboxylic acid, laureth-4 carboxylic Acid, laureth-5 carboxylic acid, laureth-6 carboxylic acid, laureth-8 carboxylic acid, laureth-10 carboxylic acid, laureth-11 carboxylic acid, laureth-12 carboxylic acid, laureth-13 carboxylic acid, laureth-14 carboxylic acid, laureth-17 carboxylic acid, PPG-6-laureth-6 carboxylic acid, PPG-8-steareth-7 carboxylic acid, myreth-3 carboxylic acid, myreth-5 carboxylic acid, Nonoxynol-5 carboxylic acid, nonoxynol-8 carboxylic acid, Nonoxynol-10 carboxylic acid, octeth-3 carboxylic acid, octoxynol-20 carboxylic acid, oleth-3 carboxylic acid, oleth-6 carboxylic acid, oleth-10 carboxylic acid, PPG-3-deceth-2 carboxylic acid, capryleth-2 carboxylic acid, Ceteth-13 carboxylic acid, deceth-2 carboxylic acid, hexeth-4 carboxylic acid, isosteareth-6 carboxylic acid, isosteareth-11 carboxylic acid, trudeceth-3 carboxylic acid, trideceth-6 carboxylic acid, trideceth-8 carboxylic acid, trideceth-12 carboxylic acid, trideceth-3 carboxylic acid, trideceth-4 carboxylic acid, trideceth-7 carboxylic acid, trideceth-15 carboxylic acid, trideceth-19 carboxylic acid, undeceth-5 carboxylic acid and combinations thereof.

The total amount of the one or more nonionic surfactants, if present, will vary. Nonetheless, the hair treatment serum typically includes from about 0.01 to about 5 wt. % of one or more nonionic surfactants. In further embodiments, the hair treatment serum includes about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. % of one or more nonionic surfactants, based on the total weight of the hair treatment serum. Preferably, the hair treatment serum includes from about 0.01 to about 5 wt. %, more preferably from about 0.05 to about 3 wt. %, and even more preferably from about 0.1 to about 2 wt. % of one or more nonionic surfactants, based on the total weight of the hair treatment serum.

(e)(ii) Cationic Surfactants

The term "cationic surfactant" is a surfactant that may be positively charged when contained in the hair treatment serum. The cationic surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In various embodiments, the one or more cationic surfactants are selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, and mixtures thereof.

Cationic surfactants include polyoxyalkylenated, primary, secondary or tertiary fatty amines, or salts thereof, and quaternary ammonium salts, and mixtures thereof, for example, chloride salts of quaternary ammonium compounds. The fatty amines generally comprise at least one $C_8$-$C_{30}$ hydrocarbon-based chain.

Nonlimiting examples of cationizable cationic surfactants include stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, and dibehenylpropyl hydroxyethylamine.

Cationizable surfactants may be chosen from fatty alkylamines and fatty dialkylamines. Preferable fatty dialkylamines include fatty amidoamine compounds, their salts, and mixtures thereof. Nonlimiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

In some instances, the cationic surfactant is preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof. In a particularly preferred embodiment, the one or more cationic surfactants are selected from cetrimonium chloride, behentrimonium chloride, behentrimonium methosulfate, stearamidopropyl dimethylamine, and a mixture thereof. More preferably, the one or more cationic surfactants are selected from cetrimonium chloride, behentrimonium chloride, mixtures thereof.

The total amount of the one or more cationic surfactants, if present, will vary. Nonetheless, the hair treatment serum typically includes from about 0.01 to about 5 wt. % of one or more cationic surfactants. In further embodiments, the hair treatment serum includes about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. % of one or more cationic surfactants, based on the total weight of the hair treatment serum. Preferably, the hair treatment serum includes from about 0.01 to about 5 wt. %, more preferably from about 0.05 to about 3 wt. %, and even more preferably from about 0.1 to about 2 wt. % of one or more cationic surfactants, based on the total weight of the hair treatment serum.

(e)(iii) Amphoteric Surfactants

Nonlimiting examples of amphoteric surfactants include alkyl amphoproprionates, betaines, alkyl sultaines, alkyl amphoacetates, and combinations thereof. In some instances, it is preferable to include one or more alkyl betaines. Nonlimiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a combination thereof. Nonlimiting examples of betaines include coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and combinations thereof. Nonlimiting examples of alkyl sultaines include cocamidopropyl hydroxysultaine and lauryl hydroxysultaine. A nonlimiting example of an alkyl amphoacetate is sodium lauroamphoacetate. In a preferred embodiment, the hair treatment serum includes one or more betaine surfactants, for example, coco betaine.

The total amount of the one or more amphoteric surfactants, if present, will vary. Nonetheless, the hair treatment serum typically includes from about 0.01 to about 5 wt. % of one or more amphoteric surfactants. In further embodiments, the hair treatment serum includes about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. % of one or more amphoteric surfactants, based on the total weight of the hair treatment serum. Preferably, the hair treatment serum includes from about 0.01 to about 5 wt. %, more preferably from about 0.05 to about 3 wt. %, and even more preferably from about 0.1 to about 2 wt. % of one or more amphoteric surfactants, based on the total weight of the hair treatment serum.

(e)(iv) Anionic Surfactants

Anionic surfactants have a fatty group and a negatively charged head group that allows them to easily interact with water molecules and reduce surface between the water and fatty substances. Alkyl sulphates, in particular, sodium lauryl sulphate (SLS) and sodium laureth sulphate (SLES), are particularly common anionic surfactants. Nonlimiting examples of anionic surfactants include sulfate-based surfactants, acyl isethionate surfactants, acyl amino acid surfactants (such as acyl taurate surfactants, acyl glycinate surfactants, acyl glutamate surfactants, and acyl sarcosinate surfactants), alkyl sulfonates, alkyl sulfosuccinates, alkyl sulfoacetates, alkoxylated monoacids, salts thereof, and mixtures thereof.

The hair treatment serum may include one or more anionic surfactants or may be free or essentially free from one or more anionic surfactants. If present, the total amount of the one or more anionic surfactants is typically from about 0.01 to about 5 wt. %, based on the total weight of the hair treatment serum. In further embodiments, the hair treatment serum includes about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. % of one or more anionic surfactants, based on the total weight of the hair treatment serum. Preferably, the hair treatment serum includes from about 0.01 to about 5 wt. %, more preferably from about 0.05 to about 3 wt. %, and even more preferably from about 0.1 to about 2 wt. % of one or more anionic surfactants, based on the total weight of the hair treatment serum.

(f) Cationic Conditioning Polymers

As the name suggests, a "cationic conditioning polymer" is a polymer having a cationic charge the provides conditioning and anti-static properties to hair. The cationic conditioning polymers may also impart thickening properties to the hair treatment serum. Therefore, in some instances, overlap exists between the one or more thickening agents and the one or more cationic conditioning polymers. For purposes of the instant disclosure, however, a single compound in a hair treatment serum does not simultaneously qualify as both a thickening agent and a cationic conditioning polymer, even though it has properties of both. For example, guar hydroxypropyltrimonium chloride is a cationic guar that provides thickening properties to composition and also provides conditioning properties to hair. If a hair treatment serum includes guar hydroxypropyltrimonium chloride, the guar hydroxypropyltrimonium chloride may be characterized as the thickening agent or characterized as the cationic conditioning polymer but does not serve simultaneously as both the thickening agent and the cationic conditioning polymer.

Nonlimiting examples of cationic conditioning polymers include copolymers of 1-vinyl-2-pyrrolidine and 1-vinyl-3-methyl-imidazolium salt (e.g., chloride salt) (referred to as polyquaternium-16); copolymers of 1-vinyl-2-pyrrolidine and dimethylaminoethyl methacrylate (referred to as polyquaternium-11); cationic diallyl quaternary ammonium-containing polymer including, for example, dimethyldiallyammonium chloride homopolymer and copolymers of acrylamide and dimethyldiallyammonium chloride (referred to as polyquaternium-6 and polyquaternium-7); polysaccharide polymers, such as cationic cellulose derivatives and cationic starch derivatives. Cationic cellulose is available as salts of hydroxyethyl cellulose reacted with trimethyl ammonium substituted epoxide (referred to as polyquaternium-10). Another type of cationic cellulose includes the polymeric quaternary ammonium salts of hydroxyethyl cellulose reacted with lauryl dimethyl ammonium-substituted epoxide (referred to as polyquaternium-24). Additionally, or alternatively, the cationic conditioning polymers may include or be chosen from cationic guar gum derivatives, such as guar hydroxypropyltrimonium chloride.

In certain embodiments, the one or more cationic conditioning polymers include cationic polysaccharide polymers, such as cationic cellulose, cationic starch, and cationic guar gum. In the context of the instant disclosure cationic polysaccharide polymers include cationic polysaccharides and polysaccharide derivatives (e.g., derivatized to be cationic), for example, resulting in cationic cellulose (cellulose derivatized to be cationic), cationic starch (derivatized to be cationic), cationic guar (guar derivatized to be cationic). Nonlimiting examples of cationic celluloses include hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, polyquaternium-10, polyquaternium-24, and mixtures thereof, preferably polyquaternium-10, polyquaternium-24, and mixtures thereof.

Nonlimiting examples of cationic guar include guar hydroxypropyltrimonium chloride, hydroxypropyl guar hydroxypropyltrimonium chloride, and mixtures thereof.

Nonlimiting examples of cationic starch include starch hydroxypropyltrimonium chloride, hydroxypropyl oxidized starch PG trimonium chloride, and a mixture thereof.

In a preferred embodiments, the one or more cationic conditioning polymers are selected from polyquaterniums. Nonlimiting examples of polyquaterniums include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-4, polyquaternium-10, polyquaternium-11, polyquaternium-67, or mixture thereof. Preferably, the hair treatment serum includes polyquaternium-4.

The total amount of the one or more cationic conditioning polymers in the hair treatment serum will vary. Nonetheless, the hair treatment serum typically includes from about 0.01 to about 5 wt. % of one or more cationic conditioning polymers. In further embodiments, the hair treatment serum includes about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, about 0.1 to about 1 wt. %, about 0.2 to about 5 wt. %, about 0.2 to about 3 wt. %, about 0.2 to about 2 wt. %, about 0.2 to about 1 wt. % of one or more cationic conditioning polymers, based on the total weight of the hair treatment serum. Preferably, the hair treatment serum includes from about 0.05 to about 3 wt. %, more preferably from about 0.1 to about 2 wt. %, and even more preferably from about 0.2 to about 1 wt. % of one or more cationic conditioning polymers.

(g) Miscellaneous Ingredients

The hair treatment serum optionally includes one or more miscellaneous ingredients. Miscellaneous ingredients are ingredients that are compatible with the hair treatment serum and do not disrupt or materially affect the basic and novel properties of the hair treatment serum. Miscellaneous ingredients commonly used in cosmetics and hair care products are known in the art. Nonlimiting examples include preservatives, fragrances, pH adjusters, salts, chelating agents, buffers, antioxidants, flavonoids, vitamins, botanical extracts, UV filtering agents, proteins, protein hydrolysates, emollients, humectants, hydrotropes, fillers (e.g., organic or inorganic, such as talk, calcium carbonate, dextrin, silica, etc.), pearlescent agents, composition colorants, etc.

In the context of the instant disclosure, a "composition colorant" is a compound that colors the composition but does not have an appreciable coloring effect on hair. In other words, the composition colorant is included to provide a coloring to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair.

In addition to the nonlimiting list of miscellaneous ingredients set forth above, components described as optional throughout the instant disclosure may be characterized as miscellaneous ingredients if not expressly set forth as a required component of the hair treatment serum. Thus, the term "miscellaneous ingredient" is understood as a catch-all phrase representing additional components that may optionally be present in amounts designated for the miscellaneous ingredients.

The total amount of miscellaneous ingredients in the hair treatment serum, if present, will vary. Nonetheless, the hair treatment serum typically includes from about 0.01 to about 10 wt. % of one or more miscellaneous ingredients, based on the total weight of the hair treatment serum. In further embodiments, the hair treatment serum includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, or about 1 to about 3 wt. % of one or more miscellaneous ingredients, based on the total weight of the hair treatment serum.

Methods for Treating Hair

As its name suggests, the hair treatment serum is particularly useful in methods for treating hair, especially human hair of the head. The hair treatment serum is useful as both a rinse-off product and a leave-on products. A "rinse-off" product refers to a composition that is rinsed and/or washed from the hair with water either after or during the application of the composition onto the hair, and before drying and/or styling the hair. At least a portion of the composition is removed from the hair during the rinsing and/or washing. A "leave-on" product refers to a composition that is not rinsed and/or washed from the hair after or during application of the composition onto the hair. The composition remains on the hair during drying and/or throughout styling.

Methods of using the hair treatment composition include methods for caring for hair, methods for conditioning hair, methods for hydrating or moisturizing hair, methods for smoothing hair, methods for reducing frizz of hair, and methods for enhancing shine of hair. The methods include applying an effective amount of the hair treatment serum to the hair. For example, the hair treatment serum may be applied to hair in need of conditioning, hair in need of hydration or moisturization, hair in need of smoothing, hair susceptible to frizz or hair suffering from frizz, hair in need of shine, or a combination thereof. Moreover, a preferred embodiment, the hair treatment serum is applied to damaged hair, for example, damaged hair in need of strengthening, in need of hydrating or moisturizing, in need of conditioning, in need of smoothing, in need of frizz control, or combinations thereof.

In a preferred embodiment, the hair treatment serum is applied to wet or damp hair, for example, freshly washed and optionally conditioned hair. After rinsing a shampoo and optionally rinsing a conditioner from the hair, while the hair remains wet or damp, an effective amount of the hair treatment serum is applied to the wet or damp hair. Upon application, the hair treatment serum can be massaged, combed, or otherwise spread throughout the hair and the scalp. Preferably, the hair treatment serum is spread throughout the totality of the hair, including to the ends of the hair. After the hair treatment serum has been spread throughout the hair, it can be rinsed from the hair or the hair can be cleansed with a shampoo and optionally treated with a conditioner. In this embodiment, the hair treatment serum is a rinse-out product. Before rinsing the hair treatment serum from the hair or shampooing the hair, the hair treatment serum is preferably allowed to remain on the hair for a period of time, for example, for about 30 second to about 30 minutes. The period of time may also be from about 1 minute to about 30 minutes, about 1 minute to about 15 minutes, about 1 minute to about 10 minutes, about 1 minute to about 5 minutes, or about 5 minutes to about 15 minutes.

Preferably, the hair treatment serum is not rinsed or cleansed from the hair but is applied as a leave-on product. After spreading the hair treatment serum throughout the wet or damp hair, the hair treatment serum is not rinsed or cleansed from the hair. Instead, the hair upon which the hair treatment serum is applied, is allowed to dry or is forcibly dried, for example, using a blow drying and the hair is styled. Alternatively, the hair may be styled while still wet or damp and subsequently dried.

PREFERRED EMBODIMENTS

In a preferred embodiment, the hair treatment serum comprises, consists essentially of, or consist of:

(a) about 0.05 to about 2 wt. %, preferably about 0.1 to about 2 wt. %, more preferably about 0.1 to about 1 wt. % of polyglutamic acid, a salt thereof, or a mixture thereof, wherein preferably, the polyglutamic acid, a salt thereof, or a mixture thereof is selected from α-polyglutamic acid, γ-polyglutamic acid, salts thereof, or mixtures thereof, more preferably wherein the polyglutamic acid is a γ-polyglutamic acid, salt thereof, or mixture thereof, for example, selected from γ-polyglutamic acid, sodium γ-polyglutamate, potassium γ-polyglutamate, calcium γ-polyglutamate, magnesium γ-polyglutamate, zinc γ-polyglutamate, or combinations thereof, more preferably, wherein the γ-polyglutamic acid, a salt thereof, or a mixture thereof is sodium γ-polyglutamate, potassium γ-polyglutamate, or a mixture thereof;

(b) about 2 to about 15 wt. %, preferably about 2 to about 10 wt. %, more preferably about 4 to about 8 wt. % of at least three oils, wherein the at least three oils comprise:

(i) about 0.1 to about 5 wt. %, preferably about 0.2 to about 3 wt. %, more preferably about 0.5 to about 2 wt. % of one or more hydrocarbon oils, wherein preferably, the one or more hydrocarbon oils are selected from undecane, tridecane, tetradecane, pentadecane, hexadecane, octadecane, docosane, squalane, hydrogenated polyisobutene, polybutene, hydrogenated polydecene, hydrogenated didecene, mineral oil, liquid, petrolatum, dodecane, isododecane, isoeicosane, isohexadecane, isoparaffin, isodecanefarnesene, hydrogenated farnesene, coconut alkanes, coconut/palm kernel alkanes, C9-C12 alkane, C10-C13 alkane, alkane, C12-C17 alkane, C13-C15 alkane, C13-15 alkane, C13-14 alkane, C14-17 alkane, C14-19 alkane, C15-19 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C11-C16 isoalkane, C12-C20 isoalkane, C13-C14 isoalkane, C13-C16 isoalkane, C14-C16 isoalkane, C15-C19 isoalkane, liquid paraffin, C12-15 alcohol benzoates or mixtures thereof, preferably wherein the one or more hydrocarbon oils is selected from C13-15 alkane, hydrogenated polydecene, hydrogenated polyisobutene, isododecane, isohexadecane, squalane, undecane, tridecane, C13-14 alkane, C14-17 alkane, C14-19 alkane, C15-19 alkane, liquid paraffin, C12-15 alcohol benzoates or mixtures thereof, wherein even more preferably wherein the one or more hydrocarbon oils is selected from squalane, liquid paraffin, C12-15 alcohol benzoates, hydrogenated polyisobutene, and hydrogenated polydecene;

(ii) about 0.1 to about 10 wt. %, preferably about 1 to about 8 wt. %, more preferably about 1 to about 5 wt. % of one or more silicone oils, wherein preferably, the one or more silicone oils are selected from caprylyl methicone, cyclohexasiloxane, cyclopentasiloxane, dimethiconol, dimethicone, methyl trimethicone, diphenyl dimethicone, diphenylsiloxy phenyl trimethicone, phenyl trimethicone, amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, or combinations thereof, wherein preferably, the one or more silicone oils is selected from cyclopentasiloxane, dimethiconol, dimethicone, amodimethicone, or mixtures thereof, and even more preferably wherein the one or more silicone oils comprises or consists of dimethicone and amodimethicone; and (iii) about 1 to about 10 wt. %, preferably about 1 to about 8 wt. %, more preferably about 2 to about 5 wt. % of one or more ester oils, preferably wherein the one or more ester oils are selected from cetyl ethylhexanoate, hexyldecyl ethylhexanoate, isocetyl myristate, isotridecyl isononanoate, pentaerythrityl tetraisostearate, pentaerythrityl tetraethylhexanoate, triethylhexanoin, caprylic/capric triglyceride, cococaprylate/caprate, dicaprylyl carbonate, phytosteryl/octyldodecyl lauroyl glutamate, trimethylolpropane tricaprylate/tricaprate, dipentaerythrityl hexa C5-9 acid esters, diisostearyl malate, hexyl laurate, neopentyl glycol diheptanoate, ethyl isostearate, isopropyl myristate, isostearyl isostearate, octyldodecyl myristate, diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, octyldodecyl myristate, 2-hexyldecyl myristate, myristyl myristate, hexyldecyl dimethyloctanoate, ethyl laurate, hexyl laurate, diisostearyl malate, dicaprylyl carbonate, and mixtures thereof, wherein more preferably, the one or more ester oils are selected from isopropyl myristate, isopropyl palmitate, isopropyl laurate, isopropyl lanolinate, isopropyl ricinoleate, isopropyl stearate, isononyl nonanoate, alkyl benzoate, dicaprylyl carbonate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, or mixtures thereof, wherein isopropyl myristate is particularly preferred;

wherein (a) and (b)(i) are in a weight ratio of about 1:1 to about 1:25, preferably a weight ratio of about 1:1 to about 1:10, and more preferably a weight ratio of about 1:2 to about 1:5;

(c) about 0.1 to about 5 wt. %, preferably about 0.2 to about 4 wt. %, more preferably about 0.5 to about 3 wt. % of at least two thickening agents, wherein the at least two thickening agents comprise:

(i) about 0.05 to about 5 wt. %, preferably about 0.1 to about 3 wt. %, more preferably about 0.2 to about 2 wt. % of one or more polyacrylic acids thickening agents, preferably one or more crosslinked polyacrylic acid thickening agents, wherein more preferably, the one or more polyacrylic acid thickening agents are selected from carbomers; and (ii) about 0.05 to about 8 wt. %, preferably about 0.1 to about 5 wt. %, more preferably about 0.5 to about 3 wt. % of one or more polysaccharide thickening agents, wherein preferably, the one or more polysaccharide thickening agents are selected from inulins, inulin derivatives, celluloses, cellulose derivatives, starches, starch derivatives, guar gums, guar derivatives, xanthan gums, xanthan derivatives, pullulan gums, pullulan derivatives alginate gums, alginate derivatives, agar-agar gums, agar derivatives, carrageenan gums, carrageneenan derivatives, gellan gums, gellan derivatives, gum Arabics, and gum Arabic derivatives, xyloses, xylose derivatives tragacanth gums, tragacanth derivatives, and combinations thereof, wherein more preferably, the one or more polysaccharide thickening agents are selected from celluloses, cellulose derivatives, guar gum, guar derivatives, starch, modified starch, and derivatives of starch, and more preferably selected from guar gum, guar derivatives, starch, modified starch, starch derivatives, and mixtures thereof selected from hydroxypropyl guar, guar hydroxypropyltrimonium chloride, hydroxypropyl guar hydroxypropyltrimonium chloride, methylhydroxypropyl starch, potato starch, wheat starch, rice starch, starch cross-linked with octenyl succinic anhydride starch oxide, dialdehyde starch, dextrin, British gum, acetyl starch, starch phosphate, carboxymethyl starch, hydroxyethyl starch, hydroxypropyl starch, and mixtures thereof;

wherein (a) and (c)(i) are in a weight ratio of about 1:1 to about 25:1, preferably a weight ratio of about 1:1 to about 1:10, and more preferably a weight ratio of about 1:2 to about 1:5;

(d) about 65 to about 95 wt. %, preferably about 70 to about 92 wt. %, more preferably about 75 to about 90 wt. % of water;

(e) about 0.05 to about 8 wt. %, preferably about 0.1 to about 6 wt. %, more preferably about 0.1 to about 5 wt. % of one or more surfactants, wherein preferably, the one or more surfactants are selected from cationic surfactants, nonionic surfactants, amphoteric surfactants, or mixtures thereof, more preferably wherein the one or more surfactants include one or more cationic surfactants, one or more nonionic surfactants, and optionally, one or more amphoteric surfactants; and (f) optionally, about 0.01 to about 5 wt. %, preferably about 0.05 to about 4 wt. %, more preferably about 0.1 to about 2 wt. % of one or more cationic conditioning polymers, preferably wherein the one or more cationic conditioning polymers are selected from polyquaterniums, wherein more preferably, the one or more cationic conditioning polymers are selected from polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-4, polyquaternium-10, polyquaternium-11, polyquaternium-67, or mixture thereof, and even more preferably wherein at least one of the one or more cationic conditioning polymers is polyquaternium-4;

(g) optionally, about 0.01 to about 10 wt. %, preferably about 0.1 to about 8 wt. %, more preferably about 1 to about 6 wt. % of one or more miscellaneous ingredients, wherein preferably the one or more miscellaneous ingredients are selected from preservatives, fragrances, pH adjusters, salts, chelating agents, buffers, antioxidants, flavonoids, vitamins, botanical extracts, UV filtering agents, proteins, protein hydrolysates, emollients, humectants, hydrotropes, fillers (e.g., organic or inorganic, such as talk, calcium carbonate, dextrin, silica, etc.), pearlescent agents, composition colorants, or mixtures thereof;

wherein the hair treatment serum is an oil-in-water emulsion or an oil-in-water dispersion, and all percentages by weight are based on a total weight of the hair treatment serum.

Moreover, it can be beneficial for the weight ratio of the one or more hydrocarbon oils of (b)(i) to the one or more polyacrylic acid thickening agents of (c)(i) to be from about 1:5 to about 5:1, preferably from about 1:3 to about 3:1, more preferably from about 1:2 to about 2:1 ((b)(i):(c)(i)).

In a preferred embodiment, the hair treatment serum is free or essentially free from fatty alcohols.

In a preferred embodiment, the hair treatment serum is free or essentially free from hyaluronic acid, salts thereof, and combinations thereof.

In a preferred embodiment, the hair treatment serum is free or essentially free from anionic surfactants.

The pH of the hair treatment serum will vary. Nonetheless, it typically has an acidic pH, i.e., a pH of less than 7. Hair itself is naturally acidic, having a pH from about 3.5 to about 4.5. The natural pH of the scalp is roughly about 5.5, which is slightly higher than the pH of the hair. The acidic pH of the hair treatment serum is useful for maintaining the natural pH of the hair and scalp, which is optimal. Various treatments to hair such as oxidative coloring, bleaching, chemical shaping, and even shampooing can disrupt the natural pH of the hair and scalp, and lead to dryness, frizz, and even dandruff. Preferably, the pH of the hair treatment serum is from about 4.5 to about 6.5, more preferably from about 5 to about 6.5, and even more preferably from about 5.5 to about 6.5.

The viscosity of the hair treatment serum will vary. Nonetheless, in certain embodiments, the viscosity of the hair treatment serum is from about 10 to about 20,000 cP at 25° C. measured with a Brookfield DV-LL+ Pro Viscometer using Helipath Spindle T-C 93 and rotational speed of 5% RPM. The viscosity of the hair treatment serum is preferably from about 100 to about 15,000 cP, more preferably from about 1,000 to about 12,000 cP, and even more preferably from about 5,000 to about 10,000 cP at 25° C. measured with a Brookfield DV-LL+ Pro Viscometer using Helipath Spindle T-C 93 and rotational speed of 5% RPM.

In a preferred embodiment, the hair treatment serum comprises, consists essentially of, or consist of:

(a) about 0.05 to about 2 wt. %, preferably about 0.1 to about 2 wt. %, more preferably about 0.1 to about 1 wt. % of sodium γ-polyglutamate, potassium γ-polyglutamate, or a mixture thereof;

(b) about 2 to about 15 wt. %, preferably about 2 to about 10 wt. %, more preferably about 4 to about 8 wt. % of at least three oils, wherein the at least three oils comprise:

(i) about 0.1 to about 5 wt. %, preferably about 0.2 to about 3 wt. %, more preferably about 0.5 to about 2 wt. % of one or more hydrocarbon oils, wherein preferably the one or more hydrocarbon oils are selected from undecane, tridecane, tetradecane, pentadecane, hexadecane, octadecane, docosane, squalane, hydrogenated polyisobutene, polybutene, hydrogenated polydecene, hydrogenated didecene, mineral oil, liquid, petrolatum, dodecane, isododecane, isoeicosane, isohexadecane, isoparaffin, isodecanefarnesene, hydrogenated farnesene, liquid paraffin, C12-15 alcohol benzoates, hydrogenated polyisobutene, and hydrogenated polydecene wherein even more preferably wherein the one or more hydrocarbon oils is selected from squalane, liquid paraffin, C12-15 alcohol benzoates, hydrogenated polyisobutene, and hydrogenated polydecene, and even more preferably wherein the one or more hydrocarbon oils is squalane;

(ii) about 0.1 to about 10 wt. %, preferably about 1 to about 8 wt. %, more preferably about 1 to about 5 wt. % of one or more silicone oils, wherein preferably, the one or more silicone oils are selected from caprylyl methicone, cyclohexasiloxane, cyclopentasiloxane, dimethiconol, dimethicone, methyl trimethicone, diphenyl dimethicone, diphenylsiloxy phenyl trimethicone, phenyl trimethicone, amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, or mixtures thereof, wherein preferably, the hair treatment compositions includes at least two silicones, wherein the at least two silicones comprise or consists of dimethicone and amodimethicone; and (iii) about 1 to about 10 wt. %, preferably about 1 to about 8 wt. %, more preferably about 2 to about 5 wt. % of one or more ester oils, preferably wherein the one or more ester oils are selected from isopropyl myristate, isopropyl palmitate, isopropyl laurate, isopropyl lanolinate, isopropyl ricinoleate, isopropyl stearate, isononyl nonanoate, alkyl benzoate, dicaprylyl carbonate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, or mixtures thereof, wherein isopropyl myristate is particularly preferred;

wherein (a) and (b)(i) are in a weight ratio of about 1:1 to about 1:25, preferably a weight ratio of about 1:1 to about 1:10, and more preferably a weight ratio of about 1:2 to about 1:5;

(c) about 0.1 to about 5 wt. %, preferably about 0.2 to about 4 wt. %, more preferably about 0.5 to about 3 wt. % of at least two thickening agents, wherein the at least two thickening agents comprise or consist of:

(i) about 0.05 to about 5 wt. %, preferably about 0.1 to about 3 wt. %, more preferably about 0.2 to about 2 wt. % of one or more polyacrylic acids thickening agents, preferably one or more crosslinked polyacrylic acid thickening agents, more preferably wherein the one or more polyacrylic acid thickening agents are selected from carbomers, for example, selected from carbomer 981, carbomer 934, carbomer 934P, carbomer 940, carbomer 941, carbomer 1342, polycarbophil, calcium polycarbophil, or mixtures thereof; and (ii) about 0.05 to about 8 wt. %, preferably about 0.1 to about 5 wt. %, more preferably about 0.5 to about 3 wt. % of one or more polysaccharide thickening agents, preferably at least two polysaccharide thickening agents, wherein preferably, at least one of the at least two polysaccharide thickening agents is selected from guar gum, guar derivatives, or mixtures thereof, and at least one of the at least two polysaccharide thickening agents is selected from starch, modified starch, derivatives of starch, or mixtures thereof, even more preferably wherein the hair treatment serum includes hydroxypropyl guar and at least one of starch, modified starch, derivatives of starch, or mixtures thereof, preferably wherein the hair treatment serums include hydroxypropyl guar and modified starch, for example, modified potato starch;

wherein (a) and (c)(i) are in a weight ratio of about 1:1 to about 25:1, preferably a weight ratio of about 1:1 to about 1:10, and more preferably a weight ratio of about 1:2 to about 1:5;

(d) about 65 to about 95 wt. %, preferably about 70 to about 92 wt. %, more preferably about 75 to about 90 wt. % of water;

(e) about 0.05 to about 8 wt. %, preferably about 0.1 to about 6 wt. %, more preferably about 0.1 to about 5 wt. % of one or more surfactants, wherein preferably, the one or more surfactants are selected from cationic surfactants, nonionic surfactants, amphoteric surfactants, or mixtures thereof, more preferably wherein the one or more surfactants include one or more cationic surfactants, one or more nonionic surfactants, and optionally, one or more amphoteric surfactants, wherein the one or more cationic surfactants are selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof, preferably wherein the one or more cationic surfactants are selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, and even more preferably wherein the hair treatment serum includes a combination of cetrimonium chloride and behentrimonium chloride; and (f) about 0.01 to about 5 wt. %, preferably about 0.05 to about 4 wt. %, more preferably about 0.1 to about 2 wt. % of one or more cationic conditioning polymers, preferably wherein the one or more cationic conditioning polymers are selected from polyquaterniums, wherein more preferably, the one or more cationic conditioning polymers are selected from polyquaternium-4, polyquaternium-10, polyquaternium-11, polyquaternium-67, or mixture thereof, and even more preferably wherein the one or more cationic conditioning polymers comprises or consists of polyquaternium-4;

(g) about 0.01 to about 10 wt. %, preferably about 0.1 to about 8 wt. %, more preferably about 1 to about 6 wt. % of one or more miscellaneous ingredients, wherein preferably the one or more miscellaneous ingredients are selected from preservatives, fragrances, pH adjusters, salts, chelating agents, buffers, antioxidants, flavonoids, vitamins, botanical extracts, UV filtering agents, proteins, protein hydrolysates, emollients, humectants, hydrotropes, fillers (e.g., organic or inorganic, such as talk, calcium carbonate, dextrin, silica, etc.), pearlescent agents, composition colorants, or mixtures thereof;

wherein the hair treatment serum is an oil-in-water emulsion or an oil-in-water dispersion, and all percentages by weight are based on a total weight of the hair treatment serum.

Moreover, it can be beneficial for the weight ratio of the one or more hydrocarbon oils of (b)(i) to the one or more polyacrylic acid thickening agents of (c)(i) to be from about 1:5 to about 5:1, preferably from about 1:3 to about 3:1, more preferably from about 1:2 to about 2:1 ((b)(i):(c)(i)).

In a preferred embodiment, the hair treatment serum is free or essentially free from fatty alcohols.

In a preferred embodiment, the hair treatment serum is free or essentially free from hyaluronic acid, salts thereof, and combinations thereof.

In a preferred embodiment, the hair treatment serum is free or essentially free from anionic surfactants.

The pH of the hair treatment serum will vary. Nonetheless, it typically has an acidic pH, i.e., a pH of less than 7. Hair itself is naturally acidic, having a pH from about 3.5 to about 4.5. The natural pH of the scalp is roughly about 5.5, which is slightly higher than the pH of the hair. The acidic pH of the hair treatment serum is useful for maintaining the natural pH of the hair and scalp, which is optimal. Various treatments to hair such as oxidative coloring, bleaching, chemical shaping, and even shampooing can disrupt the natural pH of the hair and scalp, and lead to dryness, frizz, and even dandruff. Preferably, the pH of the hair treatment serum is from about 4.5 to about 6.5, more preferably from about 5 to about 6.5, and even more preferably from about 5.5 to about 6.5.

The viscosity of the hair treatment serum will vary. Nonetheless, in certain embodiments, the viscosity of the hair treatment serum is from about 10 to about 20,000 cP at 25° C. measured with a Brookfield DV-LL+ Pro Viscometer using Helipath Spindle T-C 93 and rotational speed of 5% RPM. The viscosity of the hair treatment serum is preferably from about 100 to about 15,000 cP, more preferably from about 1,000 to about 12,000 cP, and even more preferably from about 5,000 to about 10,000 cP at 25° C. measured with a Brookfield DV-LL+ Pro Viscometer using Helipath Spindle T-C 93 and rotational speed of 5% RPM.

EXAMPLES

Various changes can be made in the above-compositions and methods without departing from the scope of the invention. Accordingly, it is intended that the entire disclosure in the above description and in the examples given below, is illustrative and not limiting.

Example 1

Hair Treatment Serums

TABLE 1

| | | | | Inventive | Comparative | | |
|---|---|---|---|---|---|---|---|
| | | | | A | 1 | 2 | 3 |
| | (a) | Gamma Polyglutamate | SODIUM POLYGLUTAMATE | 0.2 | 0.2 | 0.2 | |
| (b) | (i) | Hydrocarbon Oil | SQUALANE | 0.5 | 0.5 | | 0.5 |
| | (ii) | Silicone Oil | DIMETHICONE AND AMODIMETHICONE | 2.7 | 2.7 | 2.7 | 2.7 |
| | (iii) | Ester Oil | ISOPROPYL MYRISTATE | 3.5 | 3.5 | 3.5 | 3.5 |
| | | Total Oil | | 6.8 | 6.8 | 6.3 | 6.8 |
| | | Weight Ratio (a):(b)(i) | | 1:2.5 | 1:2.5 | | |
| (c) | (i) | Polyacrylic acid Thickener | CARBOMER | 0.5 | | 0.5 | 0.5 |
| | (ii) | Polysaccharide Thickener | HYDROXYPROPYL GUAR AND MODIFIED STARCH | 0.6 | 0.6 | 0.6 | 0.6 |
| | | Total Thickening Polymer | | 1 | 1 | 1 | 1 |
| | | Weight Ratio of (a):(c)(i) | | 1:2.5 | | 1:2.5 | 1:2.5 |
| | (d) | Water | WATER | QS | QS | QS | QS |
| | (e) | Surfactants | TRIDECETH-6, COCO-BETAINE, CETRIMONIUM CHLORIDE, AND BEHENTRIMONIUM CHLORIDE | 0.5 | 0.5 | 0.5 | 0.5 |
| | (f) | Cationic Conditioning Polymer | POLYQUATERNIUM-4 | 0.3 | 0.3 | 0.3 | 0.3 |
| | (g) | MISCELLANEOUS* | | ≤5 | ≤5 | ≤5 | ≤5 |
| | | pH | | 6.2 | NA | 3 | 6 |
| | | Viscosity (cP) at 25° C. [1] | | 7800 | | 10200 | 12600 |

TABLE 1-continued

| | Inventive | Comparative | | |
|---|---|---|---|---|
| | A | 1 | 2 | 3 |
| Performance Attributes | | | | |
| Wet Combing | BENCHMARK | NOT | 2 | 4 |
| Wet Smoothness | | STABLE [2] | 2 | 3 |
| Dry Combing | | | 3 | 2 |
| Dry Smoothness | | | 3 | 3 |
| Lightness | | | 4 | 3 |
| Anti-Frizz | | | 4 | 2 |

*MISCELLANEOUS: optionally, preservatives, fragrances, pH adjusters, salts, chelating agents, buffers, antioxidants, flavonoids, vitamins, botanical extracts, UV filtering agents, proteins, protein hydrolysates, emollients, humectants, hydrotropes, fillers (e.g., organic or inorganic, such as talk, calcium carbonate, dextrin, silica, etc.), pearlescent agents, composition colorants, etc.

[1] Measured at 25° C. measured with a Brookfield DV-LL + Pro Viscometer using Helipath Spindle T-C 93 and rotational speed of 5% RPM.

[2] Phase separated.

Example 2

Performance Testing

The hair treatment serums of Example 1 were tested on highly bleached hair swatches (SA45, 2.7 g, 27 cm) and compared. Each swatch was initially cleansed with a standard cleansing shampoo. After cleansing the swatches and rinsing the shampoo from the hair, excess water was removed from the hair swatches using a dry towel. Equal amounts of inventive serum A and comparative serums 1-3 were applied to different hair swatches and messaged throughout the hair fibers. Without rinsing or removing the serums from the hair, the hair swatches were blow dried and evaluated by a panel of three experts for the following characteristics: wet combing, wet smoothness, dry combing, dry smoothness, lightness, and anti-frizz. All characteristics were compared with the swatch treated with inventive serum A on a scale of 1 to 5, i.e., the swatch treated with inventive serum A was used as the benchmark and the swatches treated with the comparative serums were evaluated relative to the benchmark according to the following scale:

1 Better than the inventive serum;
2 Slightly better than the inventive serum;
3 Equivalent to the inventive serum;
4 Slightly inferior to the inventive serum; and
5 Inferior to the inventive serum.

The scores were averaged and appear in Table 1 of Example 1. Comparative serum 1 was not tested because it did not form a stable serum. Immediately upon preparation, comparative serum 1 phase separated. The data show that inventive serum A was lighter and provided more frizz control to hair than comparative serum 2. In addition, hair treated with inventive serum A was slightly easier to comb when dry (better score for dry combing) and slightly smoother than hair treated with comparative serum 2. Hair treated with inventive serum A was also easier to comb when wet (better score for wet combining) than hair treated with comparative serum 4. Also, inventive serum A provided slightly more smoothness on both wet and dry hair and slightly better frizz control to hair than comparative serum 4. A picture of the swatches is provided in the FIG. 1.

Example 3

Hair Treatment Serums

TABLE 2

| | | | | Inventive A | Comparative 4 |
|---|---|---|---|---|---|
| (a) | | Gamma Polyglutamate | SODIUM POLYGLUTAMATE | 0.2 | |
| (b) | (i) | Hydrocarbon Oil | SQUALANE | 0.5 | |
| | (ii) | Silicone Oil | DIMETHICONE AND AMODIMETHICONE | 2.7 | 2.7 |
| | (iii) | Ester Oil | ISOPROPYL MYRISTATE | 3.5 | 3.5 |
| | | Total Oil | | 6.8 | 6.3 |
| | | Weight Ratio of (a):(b)(i) | | 1:2.5 | NA |
| (c) | (i) | Polyacrylic acid Thickener | CARBOMER | 0.5 | 0.5 |
| | (ii) | Polysaccharide Thickener | HYDROXYPROPYL GUAR AND MODIFIED STARCH | 0.6 | 0.6 |
| | | Total Thickening Polymers | | 1 | 1 |
| | | Weight Ratio of (a):(c)(i) | | 1:2.5 | 1:2.5 |
| (d) | | Water | WATER | 89 | 89 |
| (e) | | Surfactants | TRIDECETH-6, COCO-BETAINE, CETRIMONIUM CHLORIDE, AND BEHENTRIMONIUM CHLORIDE | 0.5 | 0.5 |
| (f) | | Cationic Conditioning Polymer | POLYQUATERNIUM-4 | 0.3 | 0.3 |

TABLE 2-continued

| | | Inventive A | Comparative 4 |
|---|---|---|---|
| (g) | MISCELLANEOUS* | ≤5 | ≤5 |
| | pH | 6.2 | Not |
| | Viscosity (cP) at 25° C. [1] | 7800 | Measured |
| | Performance Attributes | | |
| | Softness on dry hair | 1 | Benchmark |
| | Smoothness on dry hair | 1 | |
| | Moisture on dry hair | 2 | |
| | Tactile Feel | 2 | |

*MISCELLANEOUS: optionally, preservatives, fragrances, pH adjusters, salts, chelating agents, buffers, antioxidants, flavonoids, vitamins, botanical extracts, UV filtering agents, proteins, protein hydrolysates, emollients, humectants, hydrotropes, fillers (e.g., organic or inorganic, such as talk, calcium carbonate, dextrin, silica, etc.), pearlescent agents, composition colorants, etc.
[1] Measured at 25° C. measured with a Brookfield DV-LL+ Pro Viscometer using Helipath Spindle T-C 93 and rotational speed of 5% RPM.

Example 4

Performance Testing

Figure 2:
FIG. 2 is a photograph of a hair swatch treated with an inventive serum and a hair swatch treated with a comparative serum.

The hair treatment serums of Example 3 were tested on highly bleached hair swatches (SA45, 2.7 g, 27 cm) and compared. Each swatch was initially cleansed with a standard cleansing shampoo. After cleansing the swatches and rinsing the shampoo from the hair, excess water was removed from the hair swatches using a dry towel. Equal amounts of inventive serum A and comparative serum 4 were applied to different hair swatches and messaged throughout the hair fibers. Without rinsing the serums from the hair, the hair swatches were blow dried and evaluated by a panel of three experts for the following characteristics: softness, smoothness, moisturization, and tactile feel. All characteristics were compared with the swatch treated with comparative serum 4 on a scale of 1 to 5, i.e., the swatch treated with comparative serum 4 was used as the benchmark and the swatch treated with the inventive serum A was evaluated relative to the benchmark according to the following scale:

1 Better than the comparative serum
2 Slightly better than the comparative serum
3 Equivalent to the comparative serum
4 Slightly inferior to the comparative serum
5 Inferior to the comparative serum The scores were averaged and appear in Table 2 of Example 3. The data show that hair treated with inventive serum A were softer and smoother than hair swatches treated with comparative serum B. The hair swatches treated with inventive serum A were also slightly more moisturized and had a slightly better tactile feel. A picture of the swatches is provided in the FIG. 2.

The foregoing disclosure illustrates and describes embodiments of the invention. The disclosure shows and describes only the preferred embodiments but it is understood that the invention is useable in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure. Accordingly, the description is not intended to limit the invention.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" or "a combination thereof" also relates to "mixtures thereof" or "combinations thereof." Throughout the disclosure, the term "a combination thereof" may be used following a list of elements as shown in the following example where letters A-F represent the elements: "one or more elements selected from the group consisting of A, B, C, D, E, F, and a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase "one or more elements selected from the group consisting of A, B, C, D, E, F, and a combination of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a combination thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The surfactants referred to throughout the disclosure may include those having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−10% of the indicated number. For example, an amount of "about 1 wt." can include an amount as low as 0.90 wt. % or as high as 1.1. Similarly, an amount of "about 50" can include an amount as low as 45 wt. % and as high as 55 wt. %.

Some of the various categories of ingredients identified for the hair treatment serum may overlap. In such cases where overlap may exist and the serum includes two overlapping ingredients (or more than two overlapping ingredients), an overlapping ingredient does not represent more than one claimed component. For example, a fatty acid may be construed as both an "oil" and separately as a "nonionic surfactant." If a claimed serum refers to an oil and separately to a nonionic surfactant, a single fatty acid in serum will serve as only the oil or as only as the nonionic surfactant. A single fatty acids cannot simultaneously serve as both the oil and the nonionic surfactant.

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

A "rinse-off" product refers to a composition that is rinsed and/or washed from the hair with water either after or during the application of the composition onto the hair, and before drying and/or styling the hair. At least a portion of the composition is removed from the hair during the rinsing and/or washing.

A "leave-on" product refers to a composition that is not rinsed and/or washed from the hair after or during application of the composition onto the hair. The composition remains on the hair during drying and/or throughout styling.

The term "surfactant" (or "emulsifier") includes salts of the surfactant, to the extent they exist, even if not explicitly stated. In other words, whenever the disclosure refers to a surfactant (or surfactants), it is intended that salts of the surfactants are also encompassed to the extent they exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

All components positively set forth in the instant disclosure can be negatively excluded from the claims and from the compositions and methods described throughout the disclosure In other words, the cleansing compositions of the instant disclosure may be free or essentially free of any one or more of the components positively set forth in the instant disclosure for possible inclusion into the cleansing compositions.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of 1% or less by weight does not materially affect the basic and novel characteristics of the claimed invention). Similarly, when a composition is essentially free from a particular element, the composition may include 1 wt. % or less, 0.5 wt. % or less, 0.1 wt. % or less, 0.05 wt. % or less, 0.01 wt. % or less, or none of the specified material. For example, if a composition is "substantially free" or "essentially free" from ethanol, the composition may optionally include ethanol in an amount up to 1 wt. %, based on the total weight of the composition, provided an amount of 1 wt. % does not materially affect the basic and novel characteristics of the composition. Furthermore, the composition may optionally include 0.5 wt. % or less, 0.1 wt. % or less, 0.05 wt. % or less, 0.01 wt. % or less, or none of the ethanol.

All publications and patent applications cited throughout the disclosure are incorporated herein by reference in their entirety, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair treatment serum comprising:

(a) about 0.05 to about 2 wt. % of γ-polyglutamic acid, a salt thereof, or a mixture thereof;

(b) about 2 to about 10 wt. % of a plurality of oils, wherein the plurality of oils comprises:

(i) about 0.1 to about 3 wt. % of one or more hydrocarbon oils;

(ii) about 1 to about 5 wt. % of one or more silicone oils; and (iii) about 1 to about 8 wt. % of one or more ester oils;

wherein (a) and (b)(i) are in a weight ratio of about 1:1 to about 1:25;

(c) about 0.1 to about 3 wt. % of a plurality of thickening agents, wherein the plurality of thickening agents comprises:

(i) about 0.1 to about 2 wt. % of one or more polyacrylic acid homopolymers; and (ii) about 0.1 to about 3 wt. % of one or more polysaccharide thickening agents;

wherein (a) and (c)(i) are in a weight ratio of about 1:1 to about 1:25;

(d) about 65 to about 92 wt. % of water;

(e) about 0.1 to about 5 wt. % of one or more surfactants; and (f) optionally, about 0.1 to about 2 wt. % of one or more cationic conditioning polymers;

wherein the hair treatment serum is an oil-in-water emulsion or an oil-in-water dispersion, and all percentages by weight are based on a total weight of the hair treatment serum.

2. The hair treatment serum of claim 1, wherein the one or more surfactants are selected from nonionic surfactants, amphoteric surfactants, and cationic surfactants.

3. The hair treatment serum of claim 1, wherein the one or more silicone oils are selected from caprylyl methicone, cyclohexasiloxane, cyclopentasiloxane, dimethiconol, dimethicone, methyl trimethicone, diphenyl dimethicone, diphenylsiloxy phenyl trimethicone, phenyl trimethicone, amodimethicone, bis-hydroxy/methoxy amodimethicones, bis-cetearyl amodimethicone, amodimethicone, bis(C13-15 alkoxy) PG amodimethicones, aminopropyl phenyl trimethicones, and aminopropyl dimethicones.

4. The hair treatment serum of claim 1, wherein:

the polyglutamic acid, salt thereof, or mixture thereof is sodium polyglutamate;

the one or more hydrocarbon oils is squalane; and the one or more polyacrylic acid homopolymers are crosslinked polyacrylic acid homopolymers.

5. A method for treating hair comprising applying the hair treatment serum of claim 1 to the hair.

6. The method of claim 5, wherein the hair treatment serum is applied to wet or damp hair and remains on the hair while drying and optionally styling the hair.

7. The hair treatment serum of claim 1, wherein the polyglutamic acid, salt thereof, or mixture thereof is selected from γ-polyglutamic acid, sodium γ-polyglutamate, potassium γ-polyglutamate, calcium γ-polyglutamate, magnesium γ-polyglutamate, zinc γ-polyglutamate, and mixtures thereof.

8. The hair treatment serum of claim 1, wherein the one or more hydrocarbon oil are selected from undecane, tridecane, tetradecane, pentadecane, hexadecane, octadecane, docosane, squalane, hydrogenated polyisobutene, polybutene, hydrogenated polydecene, hydrogenated didecene, mineral oil, liquid, petrolatum, dodecane, isododecane, isoeicosane, isohexadecane, isoparaffin, isodecane-farnesene, hydrogenated farnesene, coconut alkanes, coconut/palm kernel alkanes, C9-C12 alkane, C10-C13 alkane, alkane, C12-C17 alkane, C13-C15 alkane, C13-15 alkane, C13-14 alkane, C14-17 alkane, C14-19 alkane, C15-19 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C11-C16 isoalkane, C12-C20 isoalkane, C13-C14 isoalkane, C13-C16 isoalkane, C14-C16 isoalkane, and C15-C19 isoalkane.

9. The hair treatment serum of claim 1, wherein the one or more polysaccharide thickening agents are selected from cellulose, cellulose derivatives, guar gum, guar derivatives, starch, and modified starch.

10. The hair treatment serum of claim 1, wherein the one or more surfactants comprise one or more cationic surfactants, one or more nonionic surfactants, and one or more amphoteric surfactants.

11. The hair treatment serum of claim 1 comprising the one or more cationic conditioning polymers.

12. The hair treatment serum of claim 11, wherein the one or more cationic conditioning polymers are selected from polyquaterniums.

13. The hair treatment serum of claim 1, wherein the hair treatment serum has a viscosity of about 5,000 to about 10,000 cP at 25° C. measured with a Brookfield DV-LL+ Pro Viscometer using Helipath Spindle T-C 93 at a rotational speed of 5% RPM.

14. A hair treatment serum comprising:
(a) about 0.05 to about 2 wt. % of sodium γ-polyglutamate;
(b) about 2 to about 10 wt. % of a plurality of oils, wherein the plurality of oils comprises:
(i) about 0.2 to about 2 wt. % of one or more hydrocarbon oils;
(ii) about 1 to about 5 wt. % of one or more silicone oils selected from dimethicone, amodimethicone, and a combination thereof; and
(iii) about 1 to about 8 wt. % of one or more ester oils;
wherein (a) and (b)(i) are in a weight ratio of about 1:1 to about 1:25;
(c) about 0.1 to about 3 wt. % of a plurality of thickening agents, wherein the plurality of thickening agents comprises:
(i) about 0.1 to about 2 wt. % of one or more cross-linked polyacrylic acid homopolymers; and
(ii) about 0.1 to about 3 wt. % of one or more polysaccharide thickening agents;
wherein (a) and (c)(i) are in a weight ratio of about 1:1 to about 1:25;
(d) about 65 to about 92 wt. % of water;
(e) about 0.1 to about 5 wt. % of a plurality of surfactants, wherein the plurality of surfactants are selected from cationic surfactants, nonionic surfactants, and amphoteric surfactants; and
(f) about 0.1 to about 2 wt. % of one or more polyquaterniums;
wherein the hair treatment serum is an oil-in-water emulsion or an oil-in-water dispersion,
has a pH of about 4.5 to about 6.5, and
all percentages by weight are based on a total weight of the hair treatment serum.

15. The hair treatment serum of claim 14, wherein the one or more hydrocarbon oils are selected from squalane, hydrogenated farnesene, isohexadecane, isododecane, C13-15 alkane, C15-19 alkane, coconut alkanes, coconut/palm kernel alkanes, hydrogenated polydecene, and hydrogenated polyisobutene.

16. The hair treatment composition of claim 15, wherein the one or more ester oils are selected from isopropyl myristate, isopropyl palmitate, isopropyl laurate, isopropyl lanolinate, isopropyl ricinoleate, isopropyl stearate, isononyl nonanoate, C12-15 alkyl benzoate, dicaprylyl carbonate, isopropyl isostearate, isopropyl oleate, ethylhexyl stearate, isononyl stearate, isocetyl stearate, isononyl isononanoate, isotridecyl isononanoate, cetearyl isononanoate, ethylhexyl laurate, ethylhexyl isostearate, ethylhexyl cocoate, octyldodecyl palmitate, butyl stearate, hexyl laurate, decyl oleate, oleyl oleate, oleyl erucate, erucyl oleate, and erucyl erucate.

17. The hair treatment serum of claim 16, wherein the hair treatment serum has a viscosity of about 5,000 to about 10,000 cP at 25° C. measured with a Brookfield DV-LL+ Pro Viscometer using Helipath Spindle T-C 93 at a rotational speed of 5% RPM.

18. A method for treating hair comprising applying the hair treatment serum of claim 14 to the hair.

19. The method of claim 18, wherein the hair treatment serum is applied to wet or damp hair and remains on the hair while drying and optionally styling the hair.

* * * * *